United States Patent
Ohashi

(10) Patent No.: US 11,845,006 B2
(45) Date of Patent: Dec. 19, 2023

(54) SKELETON MODEL UPDATING APPARATUS, SKELETON MODEL UPDATING METHOD, AND PROGRAM

(71) Applicant: SONY INTERACTIVE ENTERTAINMENT INC., Tokyo (JP)

(72) Inventor: Yoshinori Ohashi, Tokyo (JP)

(73) Assignee: SONY INTERACTIVE ENTERTAINMENT INC., Tokyo (JP)

( * ) Notice: Subject to any disclaimer, the term of this patent is extended or adjusted under 35 U.S.C. 154(b) by 132 days.

(21) Appl. No.: 17/618,448

(22) PCT Filed: Jul. 9, 2019

(86) PCT No.: PCT/JP2019/027120
§ 371 (c)(1),
(2) Date: Dec. 11, 2021

(87) PCT Pub. No.: WO2021/005708
PCT Pub. Date: Jan. 14, 2021

(65) Prior Publication Data
US 2022/0410000 A1    Dec. 29, 2022

(51) Int. Cl.
*A63F 13/56*        (2014.01)
*A63F 13/428*       (2014.01)
*A63F 13/213*       (2014.01)

(52) U.S. Cl.
CPC .......... *A63F 13/428* (2014.09); *A63F 13/213* (2014.09); *A63F 13/56* (2014.09)

(58) Field of Classification Search
CPC ....... A63F 13/213; A63F 13/428; A63F 13/56
See application file for complete search history.

(56) References Cited

U.S. PATENT DOCUMENTS

| | | | |
|---|---|---|---|
| 10,573,050 B1* | 2/2020 | Liu | G06T 17/20 |
| 2014/0328519 A1* | 11/2014 | Martinetz | G06T 7/251 |
| | | | 382/107 |

(Continued)

FOREIGN PATENT DOCUMENTS

| | | |
|---|---|---|
| JP | 2008-052726 A | 3/2008 |
| JP | 2014-157608 A | 8/2014 |
| WO | 2017/170264 A1 | 10/2017 |

OTHER PUBLICATIONS

International Search Report and Written Opinion dated Sep. 3, 2019, from PCT/JP2019/027120, 6 sheets.

(Continued)

*Primary Examiner* — David L Lewis
*Assistant Examiner* — Shauna-Kay Hall
(74) *Attorney, Agent, or Firm* — XSENSUS LLP

(57) ABSTRACT

A skeleton model updating apparatus, a skeleton model updating method, and a program by which time and effort for changing the pose of a skeleton model to a known standard pose can be reduced. A target node identifying section identifies target nodes from among a plurality of nodes included in a skeleton model that is in a pose other than a standard pose. A reference node identifying section identifies a reference node that is positioned closest to the side of the target nodes, from among nodes that are connected to all of the target nodes via one or more bones. A position deciding section decides positions of the target nodes such that relative positions of the target nodes with respect to the position of the reference node are adjusted to predetermined positions.

20 Claims, 14 Drawing Sheets

(56) References Cited

U.S. PATENT DOCUMENTS

2018/0122125 A1*  5/2018  Brewster .............. G06T 13/40
2019/0156564 A1*  5/2019  Tung .................... G06T 7/50
2019/0347826 A1* 11/2019  Zhang .................. G06N 3/08
2020/0250874 A1*  8/2020  Assouline ............. G06N 3/08

OTHER PUBLICATIONS

Norihide Kaneko, et al., "Motion puppetry taking skeletal similarity into account", ITE Technical Report, Mar. 2015, vol. 39, No. 14, 43-46, 4 sheets.

* cited by examiner

14

SKELETON MODEL UPDATING APPARATUS, SKELETON MODEL UPDATING METHOD, AND PROGRAM

TECHNICAL FIELD

The present invention relates to a skeleton model updating apparatus, a skeleton model updating method, and a program.

BACKGROUND ART

A body tracking technology has been known for updating a pose of a skeleton model that is linked with a user, on the basis of data indicating postures of a plurality of trackers mounted on the user.

SUMMARY

Technical Problem

For example, body tracking using a non-human skeleton model (see FIG. 17) modeling a dog, a dragon, an octopus, or the like is demanded in some cases. Such body tracking is based on a premise that a default pose of a skeleton model needs to be changed to a known standard pose such as a T-pose or an A-pose, irrespective of what the default pose is.

Since this kind of work for changing the pose of a skeleton model to a standard pose has had to be manually performed, a lot of time and effort of a worker were required.

The present invention has been made in view of the abovementioned problems, and one object thereof is to provide a skeleton model updating apparatus, a skeleton model updating method, and a program by which time and effort for changing the pose of a skeleton model to a known standard pose can be reduced.

Solution to Problem

In order to solve the abovementioned problem, a skeleton model updating apparatus according to the present invention includes a target node identifying section that identifies a plurality of target nodes from among a plurality of nodes included in a skeleton model being in a pose other than a known standard pose, a reference node identifying section that identifies a reference node positioned closest to a side of the plurality of target nodes, from among nodes connected to all of the plurality of target nodes via one or more bones, a position deciding section that decides positions of the plurality of target nodes or a position of the reference node such that relative positions of the plurality of target nodes with respect to the position of the reference node are adjusted to predetermined positions, and a pose updating section that updates the pose of the skeleton model to the standard pose on the basis of the decided positions of the target nodes.

According to one aspect of the present invention, the target node identifying section identifies, as the target nodes, a node corresponding to a left hand and a node corresponding to a right hand.

Further, according to another aspect of the present invention, the target node identifying section identifies, as the target nodes, a node corresponding to a left hand, a node corresponding to a right hand, and a node corresponding to a head part.

Further, according to still another aspect of the present invention, the target node identifying section identifies, as the target nodes, a node corresponding to a left foot and a node corresponding to a right foot.

In addition, a skeleton model updating method according to the present invention includes a step of identifying a plurality of target nodes from among a plurality of nodes included in a skeleton model that is in a pose other than a known standard pose, a step of identifying a reference node that is positioned closest to a side of the plurality of target nodes, from among nodes that are connected to all of the plurality of target nodes via one or more bones, a step of deciding positions of the plurality of target nodes or a position of the reference node such that relative positions of the plurality of target nodes with respect to the position of the reference node are adjusted to predetermined positions, and a step of updating the pose of the skeleton model to the standard pose on the basis of the decided positions of the target nodes.

In addition, a program according to the present invention causes a computer to execute a step of identifying a plurality of target nodes from among a plurality of nodes included in a skeleton model that is in a pose other than a known standard pose, a step of identifying a reference node that is positioned closest to a side of the plurality of target nodes, from among nodes that are connected to all of the plurality of target nodes via one or more bones, a step of deciding positions of the plurality of target nodes or a position of the reference node such that relative positions of the plurality of target nodes with respect to the position of the reference node are adjusted to predetermined positions, and a step of updating the pose of the skeleton model to the standard pose on the basis of the decided positions of the target nodes.

DESCRIPTION OF EMBODIMENT

Figure 1:
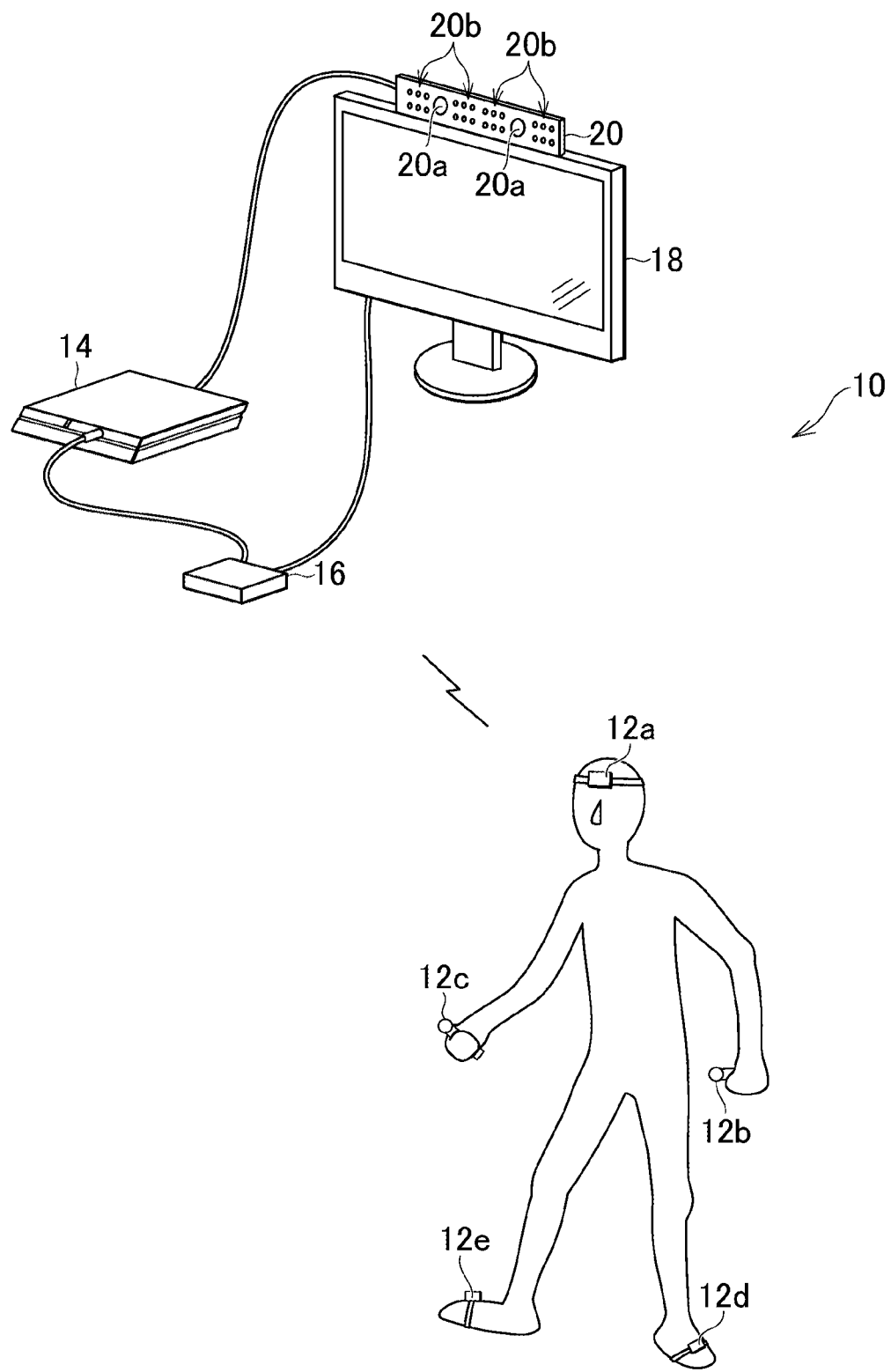
FIG. 1 is a configuration diagram illustrating one example of an entertainment system according to one embodiment of the present invention.
Figure 2:
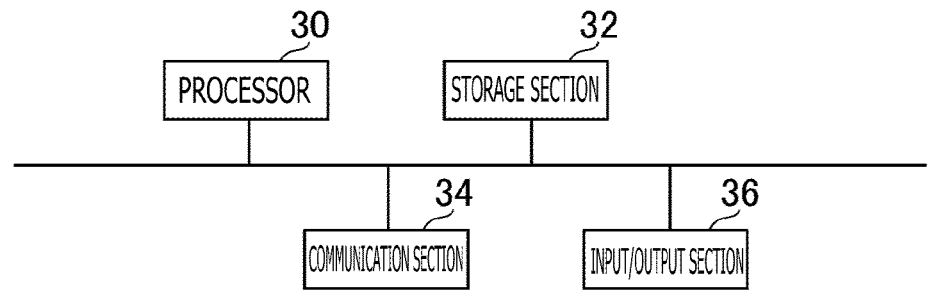
FIG. 2 is a configuration diagram illustrating one example of an entertainment apparatus according to one embodiment of the present invention.

FIG. 1 is a diagram illustrating one example of the configuration of an entertainment system 10 according to one embodiment of the present invention. FIG. 2 is a diagram illustrating one example of the configuration of an entertainment apparatus 14 according to the present embodiment.

As illustrated in FIG. 1, the entertainment system 10 according to the present embodiment includes a plurality of trackers 12 (trackers 12a to 12e in FIG. 1), the entertainment apparatus 14, a relay apparatus 16, a display 18, and a camera-and-microphone unit 20.

Each tracker 12 according to the present embodiment is a device for tracking the position and the orientation of the corresponding tracker 12, for example. Each tracker 12 may include various sensors such as a camera, an inertial sensor (inertial measurement unit (IMU)), a geomagnetic sensor (azimuth sensor), an acceleration sensor, a motion sensor, and a global positioning system (GPS) module. Each tracker 12 may identify the posture of the corresponding tracker 12 on the basis of sensing data which is a measurement result obtained by the sensors included in the tracker 12.

In addition, for example, the posture of each tracker 12 may be identified on the basis of an image that is taken by a camera 20a included in the camera-and-microphone unit 20, which will be explained later, and that includes an image of the tracker 12.

In the present embodiment, the tracker 12a, the tracker 12b, the tracker 12c, the tracker 12d, and the tracker 12e are respectively mounted on the head part, the left hand, the right hand, the left foot, and the right foot of a user. As illustrated in FIG. 1, the tracker 12b and the tracker 12c may be held in the user's hands. In the present embodiment, postures identified by the tracker 12a, the tracker 12b, the tracker 12c, the tracker 12d, and the tracker 12e each correspond to the postures of the head part, the left hand, the right hand, the left foot, and the right foot of the user. In this manner, postures of a plurality of parts of a user body are identified by a plurality of the trackers 12 in the present embodiment.

For example, the entertainment apparatus 14 according to the present embodiment is a computer such as a game console, a digital versatile disc (DVD) player, or a Blu-ray (registered trademark) player. The entertainment apparatus 14 according to the present embodiment generates a video or a sound by executing a game program stored in the apparatus or recorded in an optical disk, or by reproducing content stored in the apparatus or recorded in an optical disk, for example. Further, the entertainment apparatus 14 according to the present embodiment outputs a video signal indicating the generated video or a sound signal indicating the generated sound, to the display 18 via the relay apparatus 16.

For example, the entertainment apparatus 14 according to the present embodiment includes a processor 30, a storage section 32, a communication section 34, and an input/output section 36, as illustrated in FIG. 2.

The processor 30 is a program control device such as a central processing unit (CPU) that operates in accordance with a program installed in the entertainment apparatus 14, for example. The processor 30 according to the present embodiment includes a graphics processing unit (GPU) which renders an image on a frame buffer on the basis of data or a graphics command supplied from the CPU.

The storage section 32 is a hard disk drive or a storage element such as a read only memory (ROM) or random access memory (RAM), for example. A program, etc., to be executed by the processor 30 is stored in the storage section 32. In addition, a region of the frame buffer on which an image is rendered by the GPU is reserved in the storage section 32 according to the present embodiment.

The communication section 34 is a communication module such as a wireless local area network (LAN) module, for example.

The input/output section 36 is an input/output port such as a High-Definition Multimedia Interface (HDMI) (registered trademark) port or a universal serial bus (USB) port.

The relay apparatus 16 according to the present embodiment is a computer that relays a video signal or a sound signal outputted from the entertainment apparatus 14 and that outputs the signal to the display 18.

The display 18 according to the present embodiment is a liquid crystal display, for example. The display 18 displays, for example, a video indicated by a video signal outputted from the entertainment apparatus 14.

The camera-and-microphone unit 20 according to the present embodiment includes the camera 20a that captures an image of a subject and outputs the image to the entertainment apparatus 14 and a microphone 20b that acquires an ambient sound, transforms the sound to sound data, and outputs the sound data to the entertainment apparatus 14, for example. In addition, the camera 20a according to the present embodiment is a stereo camera.

Each tracker 12 and the relay apparatus 16 are configured to be able to wirelessly exchange data with each other, for example. The entertainment apparatus 14 and the relay apparatus 16 are connected via an HDMI cable or a USB cable, for example, and thus, are able to exchange data with each other. The relay apparatus 16 and the display 18 are connected via an HDMI cable, for example. The entertainment apparatus 14 and the camera-and-microphone unit 20 are connected via an auxiliary (AUX) cable, for example.

Figure 3:
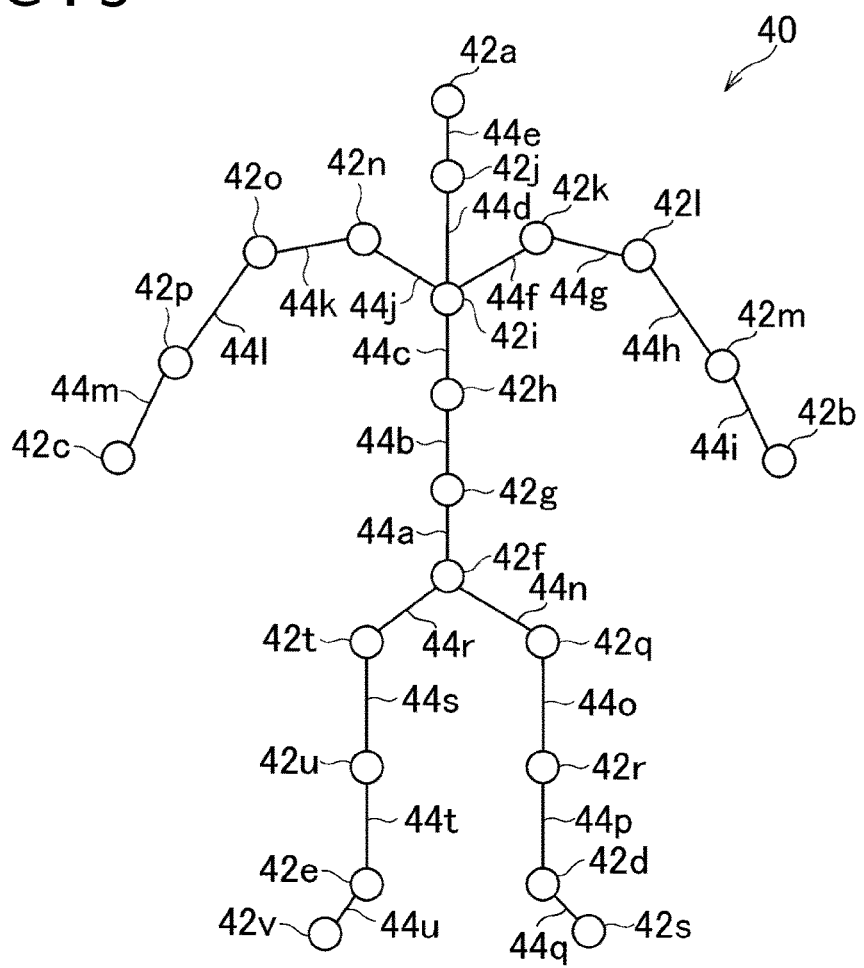
FIG. 3 is a diagram illustrating one example of a skeleton model.

According to the present embodiment, while the entertainment apparatus 14 is executing a game program, for example, various processes including a game process based on the postures of a plurality of parts of a user's body are executed in a skeleton model 40 illustrated in FIG. 3. Then, a video according to a result of the processes is displayed on the display 18, for example.

For example, a video of a polygon model of a player object is displayed on the display 18 according to the pose of the skeleton model 40.

As illustrated in FIG. 3, the skeleton model 40 according to the present embodiment includes a head node 42a, a left hand node 42b, a right hand node 42c, a left foot node 42d, and a right foot node 42e. The head node 42a corresponds to the user's head part on which the tracker 12a is mounted. The left hand node 42b corresponds to the user's left hand on which the tracker 12b is mounted. The right hand node 42c corresponds to the user's right hand on which the tracker 12c is mounted. The left foot node 42d corresponds to the user's left foot on which the tracker 12d is mounted. The right foot node 42e corresponds to the user's right foot on which the tracker 12e is mounted.

In addition to the abovementioned nodes 42, the skeleton model 40 further includes a pelvis node 42f, a first spine node 42g, a second spine node 42h, a third spine node 42i, and a neck node 42j. In the present embodiment, the pelvis node 42f serves as a root node of the entire skeleton model 40, for example. In addition, in the present embodiment, the pelvis node 42f corresponds to a node of the hip part, for example.

The skeleton model 40 further includes a left collarbone node 42k, a left upper arm node 42l, a left forearm node 42m, a right collarbone node 42n, a right upper arm node 42o, and a right forearm node 42p.

Also, the skeleton model 40 further includes a left thigh node 42q, a left calf node 42r, a left ball-of-foot node 42s, a right thigh node 42t, a right calf node 42u, and a right ball-of-foot node 42v.

As illustrated in FIG. 3, here, a bone 44a connects the pelvis node 42f and the first spine node 42g. Further, a bone 44b connects the first spine node 42g and the second spine node 42h. Further, a bone 44c connects the second spine node 42h and the third spine node 42i. Further, a bone 44d connects the third spine node 42i and the neck node 42j. Further, a bone 44e connects the neck node 42l and the head node 42a.

Further, a bone 44f connects the third spine node 42i and the left collarbone node 42k. Further, a bone 44g connects the left collarbone node 42k and the left upper arm node 42l. Further, a bone 44h connects the left upper arm node 42l and the left forearm node 42m. Further, a bone 44i connects the left forearm node 42m and the left hand node 42b.

Further, a bone 44j connects the third spine node 42i and the right collarbone node 42n. Further, a bone 44k connects the right collarbone node 42n and the right upper arm node 42o. Further, a bone 44l connects the right upper arm node 42o and the right forearm node 42p. Further, a bone 44m connects the right forearm node 42p and the right hand node 42c.

Further, a bone 44n connects the pelvis node 42f and the left thigh node 42q. Further, a bone 44o connects the left thigh node 42q and the left calf node 42r. Further, a bone 44p connects the left calf node 42r and the left foot node 42d. Further, a bone 44q connects the left foot node 42d and the left ball-of-foot node 42s.

Further, a bone 44r connects the pelvis node 42f and the right thigh node 42t. A bone 44s connects the right thigh node 42t and the right calf node 42u. A bone 44t connects the right calf node 42u and the right foot node 42e. A bone 44u connects the right foot node 42e and the right ball-of-foot node 42v.

FIG. 3 illustrates the skeleton model 40 being in a standard pose (e.g., what is generally called an A-pose with legs apart and arms diagonally down), which is the skeleton model 40 being in an initial state.

Further, in the present embodiment, body tracking based on postures identified for the plurality of trackers 12 can be conducted, for example. Here, for example, a position relative to an initial-state reference position and an orientation relative to an initial-state reference orientation are decided for each of the nodes 42 included in the skeleton model 40. In addition, an orientation relative to an initial-state reference orientation is decided for each of the bones 44 included in the skeleton model 40.

For example, the posture of the head node 42a can be decided on the basis of data indicating a posture identified for the tracker 12a. Also, the posture of the left hand node 42b can be decided on the basis of data indicating a posture identified for the tracker 12b. Also, the posture of the right hand node 42c can be decided on the basis of data indicating a posture identified for the tracker 12c. Also, the posture of the left foot node 42d can be decided on the basis of data indicating a posture identified for the tracker 12d. Also, the posture of the right foot node 42e can be decided on the basis of data indicating a posture identified for the tracker 12e.

In addition, the posture of the pelvis node 42f also can be decided on the basis of the decided posture of the head node 42a, for example. Here, for example, on the basis of postures identified for the trackers 12a to 12e, the posture of the pelvis node 42f may be estimated by using a machine learning model that has been learned. Also, the posture of the third spine node 42i may be decided in a similar manner.

On the basis of the above decision result or estimation result, it is possible to decide the positions and orientations of the remaining nodes 42 and the orientations of the bones 44 by FABRIK calculation. For example, the head node 42a, the left hand node 42b, the right hand node 42c, the left foot node 42d, and the right foot node 42e correspond to effectors in FABRIK. According to motions of the effectors, the positions and orientations of the nodes 42 and the orientations of the bones 44 included in the skeleton model 40 are decided.

Figure 4:
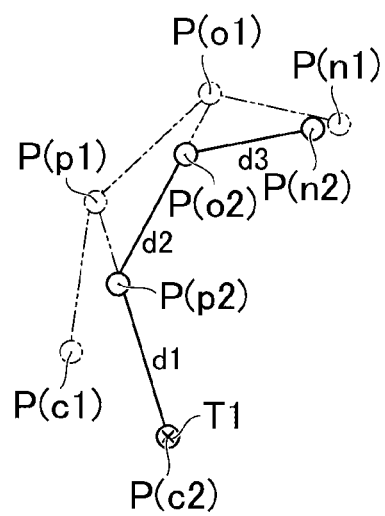
FIG. 4 is a diagram schematically illustrating one example of a forward reaching phase in forward and backward reaching inverse kinematics (FABRIK) calculation.
Figure 5:
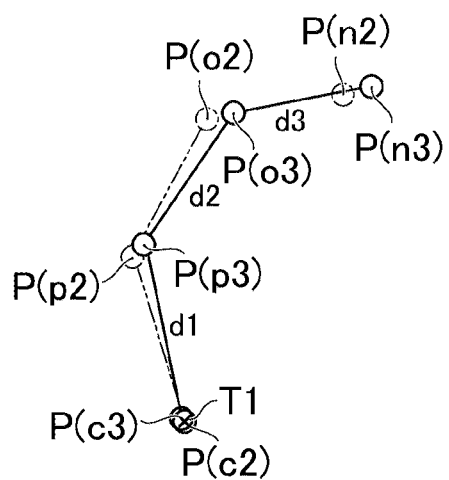
FIG. 5 is a diagram schematically illustrating one example of a backward reaching phase in FABRIK calculation.

FIGS. 4 and 5 are diagrams each schematically illustrating one example of FABRIK calculation. In each of FIGS. 4 and 5, FABRIK calculation that is carried out for the right hand node 42c, the right collarbone node 42n, the right upper arm node 42o, and the right forearm node 42p are illustrated as one example.

In FIG. 4, the current positions of the right hand node 42c, the right collarbone node 42n, the right upper arm node 42o, and the right forearm node 42p in the skeleton model 40 are respectively denoted by P(c1), P(n1), P(o1), and P(p1). The lengths of the bone 44m, the bone 44l, the bone 44k, and the bone 44j are respectively defined as d1, d2, and d3.

In this state, it is assumed that a position T1 to which the right hand node 42c is to move is identified on the basis of a measurement result obtained by the tracker 12c.

Hereinafter, a forward reaching phase in the FABRIK calculation will be explained with reference to FIG. 4.

In the forward reaching phase, first, the right hand node 42c moves to the position T1. In FIG. 4, the position of the right hand node 42c having moved is denoted by P(c2). Then, the right forearm node 42p moves to a position P(p2) that is at a distance of the length d1 away, in a direction from the position P(c2) toward the position P(p1), from the position P(c2). Then, the right upper arm node 42o moves to a position P(o2) that is at a distance of the length d2 away, in a direction from the position P(p2) toward the position P(o1), from the position P(p2). Then, the right collarbone node 42n moves to a position P(n2) that is at a distance of the length d3 away, in a direction from the position P(o2) toward the position P(n1), from the position P(o2).

Accordingly, the forward reaching phase processing in the FABRIK calculation involves deciding a new position of a parent node 42 of a node 42 being linked with a tracker 12 on the basis of a position to which the node 42 being linked with the tracker 12 is to move and the current position of the parent node 42. This decision is made on condition that the distance between the node 42 being linked with the tracker 12 and the parent node 42 is kept constant. Hereinafter, nodes 42 being linked with corresponding trackers 12 are referred to as target nodes.

Hereinafter, a backward reaching phase in the FABRIK calculation will be explained with reference to FIG. 5.

First, the right collarbone node 42n moves from the position P(n2) to a position P(n3). The position P(n3) in FIG. 5 is the same position as the position P(n1) of the right collarbone node 42n at the start time of the FABRIK calculation. Then, the right upper arm node 42o moves to a position P(o3) that is at a distance of the length d3 away, in a direction from the position P(n3) toward the position P(o2), from the position P(n3). Then, the right forearm node 42p moves to a position P(p3) that is at a distance of the length d2 away, in a direction from the position P(o3) toward the position P(p2), from the position P(o3). Then, the right hand node 42c moves to a position P(c3) that is at a distance of the length d1 away, in a direction from the position P(p3) toward the position P(c2), from the position P(p3).

Until the distance between the position of the right hand node 42c and the position T1 becomes equal to or shorter than a predetermined threshold, the forward reaching phase and the backward reaching phase are repeatedly executed. It is to be noted that, even if the distance between the position of the right hand node 42c and the position T1 does not become equal to or shorter than the predetermined threshold, the FABRIK calculation is ended after the forward reaching phase and the backward reaching phase are repeated a predetermined number of times (e.g., ten times).

In this manner, the FABRIK calculation uses a simple algorithm to decide the pose of the skeleton model 40. However, as a result of this, a joint may be inhibited from being bent to a natural direction in some cases, so that the pose of the skeleton model 40 is decided to be one that is unreal as a pose of a human body.

In addition, the pose decision based on the FABRIK calculation involves acquiring information regarding rotation of hands about respective arm directions from the tracker 12b and the tracker 12c, but this information is not reflected in rotation of elbows about the respective arm directions.

In the FABRIK calculation of the skeleton model 40 having a tree structure, forward reaching phase processing needs to be executed independently on a node group which includes the target nodes and the start points of which are set to a plurality of target nodes. Accordingly, the entire posture of the plurality of nodes 42 that are positioned around a nodal point in the skeleton model 40 having a tree structure, or positioned from the chest to the shoulders, for example may be largely distorted as a result of the forward reaching phase processing, although the entire posture of these nodes should not be distorted.

As described above, deciding the pose of the skeleton model 40 by the FABRIK calculation may offer a result with low appropriateness.

In view of these circumstances, the present embodiment achieves improvement in the appropriateness of a result of decision of the pose of the skeleton model 40 obtained by the FABRIK calculation, in the following manner.

Hereinafter, functions of the entertainment apparatus 14 according to the present embodiment and processes that are executed in the entertainment apparatus 14 according to the present embodiment will be explained in more detail.

Figure 6:
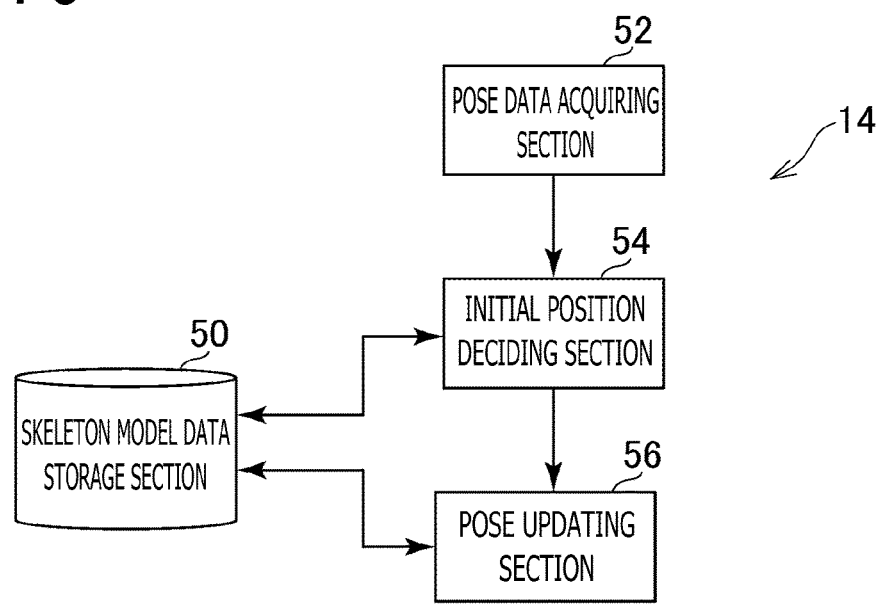
FIG. 6 is a functional block diagram illustrating one example of functions that are implemented by an entertainment apparatus according to one embodiment of the present invention.

FIG. 6 is a functional block diagram illustrating one example of functions of the entertainment apparatus 14 according to the present embodiment. It is to be noted that all the functions illustrated in FIG. 6 are not necessarily required to be implemented by the entertainment apparatus 14 according to the present embodiment, and further, any function other than those illustrated in FIG. 6 may be implemented.

As illustrated in FIG. 6, the entertainment apparatus 14 according to the present embodiment functionally includes a skeleton model data storage section 50, a pose data acquiring section 52, an initial position deciding section 54, and a pose updating section 56, for example.

The skeleton model data storage section 50 is implemented mainly by the storage section 32. The pose data acquiring section 52 is implemented mainly by the processor 30 and the input/output section 36. The initial position deciding section 54 and the pose updating section 56 are implemented mainly by the processor 30.

These functions may be implemented when the processor 30 executes a program that includes commands corresponding to these functions and that is installed in the entertainment apparatus 14 which is a computer. The program may be supplied to the entertainment apparatus 14 via a computer readable information storage medium such as an optical disk, a magnetic disk, a magnetic tape, a magneto-optical disk, or a flash memory, or via the internet, etc.

In the present embodiment, the skeleton model data storage section 50 stores skeleton model data indicating the pose of the skeleton model 40, for example. The skeleton model data may include data regarding the respective positions of the plurality of nodes 42, for example. Also, the skeleton model data may include data indicating the orientations of the nodes 42. Here, the data indicating the orientations may indicate the rotation amount in each of three axis directions, for example. Also, the skeleton model data may include data indicating the position and the orientation of each bone 44. The position and the orientation of each bone 44 are uniquely defined on the basis of the positions of the nodes 42 disposed at both ends of the bone 44.

Further, in the present embodiment, it is assumed that skeleton model data indicating the latest pose of the skeleton model 40 is stored in the skeleton model data storage section 50. Moreover, it is assumed that skeleton model data indicating an initial-state pose of the skeleton model 40 being in a standard pose such as an A-pose is also stored in the skeleton model data storage section 50.

In the present embodiment, for example, the pose data acquiring section 52 acquires pose data indicating the positions and the orientations of the trackers 12a to 12e identified at a predetermined sampling rate. Here, for example, each tracker 12 may generate the pose data indicating the position and the orientation of the tracker 12 at the predetermined sampling rate. Upon generating the pose data, the tracker 12 may transmit the generated pose data to the entertainment apparatus 14 via the relay apparatus 16. Alternatively, for example, the camera-and-microphone unit 20 may generate the pose data indicating the positions and the orientations of the trackers 12a to 12e at the predetermined sampling rate. Upon generating the pose data, the camera-and-microphone unit 20 may transmit the generated pose data to the entertainment apparatus 14.

In the present embodiment, for example, the initial position deciding section 54 decides initial positions of some of the nodes 42 on the basis of the pose data acquired by the pose data acquiring section 52.

In the present embodiment, for example, the pose updating section 56 updates the pose of the skeleton model 40. Here, for example, the skeleton model data stored in the skeleton model data storage section 50 is updated. On the basis of the pose data acquired by the pose data acquiring section 52 and the initial positions decided by the initial position deciding section 54, the pose updating section 56 may update the pose of the skeleton model 40 by FABRIK calculation.

Figure 7:
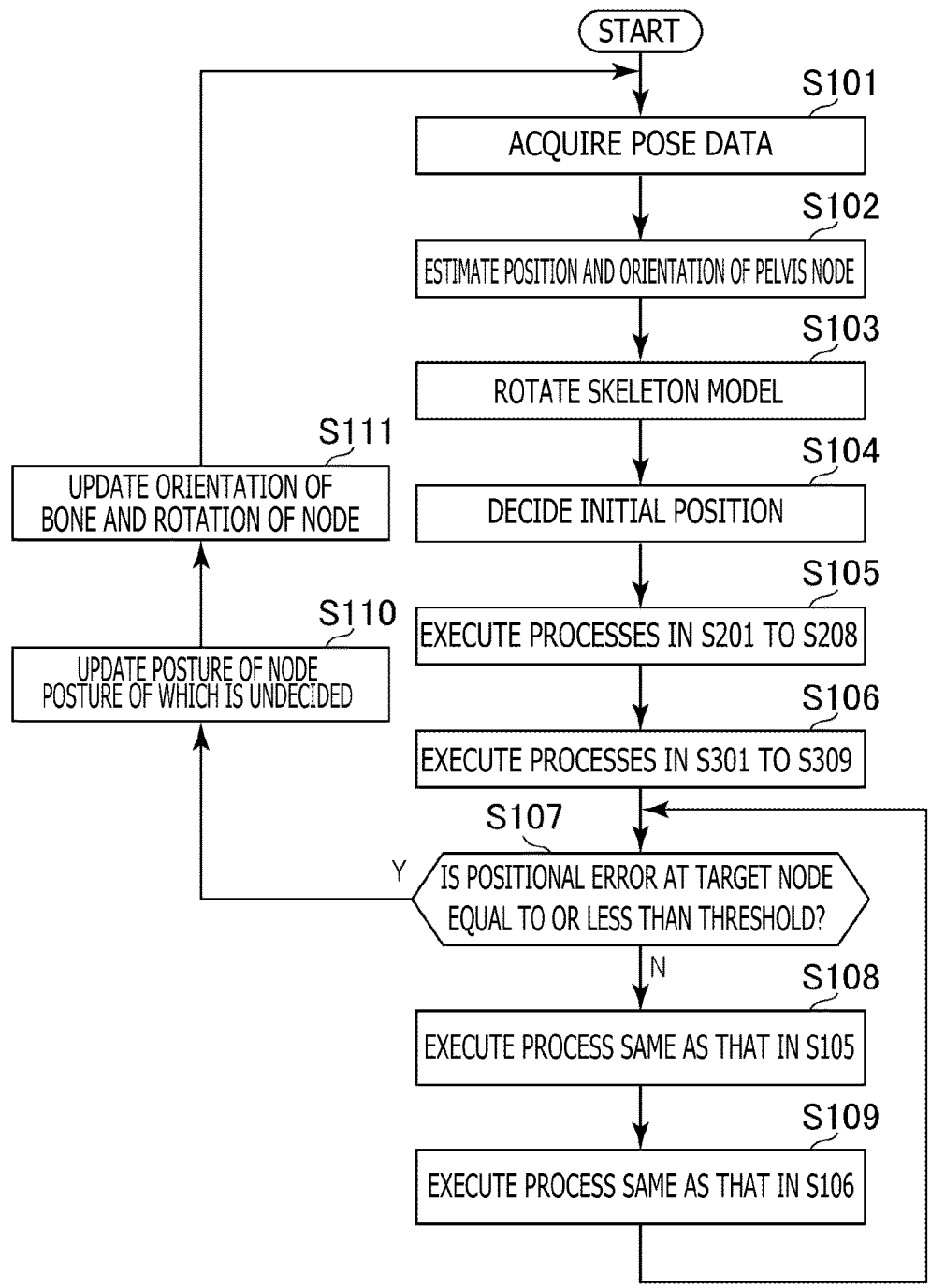
FIG. 7 is a flowchart illustrating one example of a process flow that is executed in an entertainment apparatus according to one embodiment of the present invention.

Here, one example of a process flow that is executed in the entertainment apparatus 14 according to the present embodiment will be explained with reference to a flowchart illustrated in FIG. 7.

First, the pose data acquiring section 52 acquires pose data that is generated by the trackers 12 and that indicates the positions and the orientations of the trackers 12 at a latest particular timing (S101). Here, for example, the pose data acquiring section 52 acquires pose data indicating the respective positions and orientations of the trackers 12a to 12e.

Next, the pose updating section 56 estimates the position and the orientation of the pelvis node 42f on the basis of the pose data acquired in the process illustrated in S101 (S102). Instead of the position and the orientation of the pelvis node 42f, those of the third spine node 42i may be estimated here, for example. Alternatively, the positions and the orientations of the pelvis node 42f and the third spine node 42i may be estimated, for example.

Then, the pose updating section 56 updates the skeleton model data on the basis of the estimation result obtained in the process illustrated in in S102 (S103). In S103, for example, a process of rotating the latest skeleton model 40 and the skeleton model 40 being in the initial state is executed.

Subsequently, the initial position deciding section 54 decides initial positions of some of the nodes 42 included in the skeleton model 40 (S104).

Figure 8:
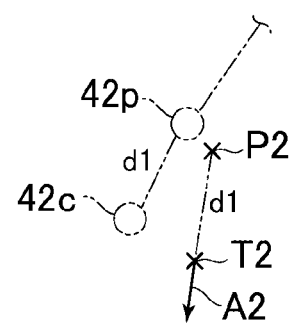
FIG. 8 is an explanatory diagram of one example of deciding an initial position of a node.

Here, on the basis of the position of the tracker 12c indicated by the pose data acquired in the process illustrated in S101, the position T2 to which the right hand node 42c which is a target node is to move and the direction A2 to which the right hand node 42c is to be oriented are identified, as illustrated in FIG. 8, for example. Subsequently, a position P2 that is at a distance of the length d1 away, in a direction along the direction A2 but opposite to the direction A2, from the position T2 is decided as an initial position of the right forearm node 42p which is the parent node 42 of the right hand node 42c. The length d1 here is the length of the bone 44m, as previously explained.

It is to be noted that a position obtained by interpolating the current position of the right forearm node 42p and the position P2 with a predetermined weight may be decided as an initial position of the right forearm node 42p.

This weight may be decided on the basis of the distance between the position T2 and the current position of the right hand node 42c, which corresponds to the speed of the tracker 12c. For example, when the distance between the position T2 and the current position of the right hand node 42c is shorter, a position closer to the current position of the right forearm node 42p may be decided as an initial position of the right forearm node 42p. Accordingly, a situation in which a player rotates only a wrist but large motion of an elbow of a player object is produced can be avoided.

Figure 9:
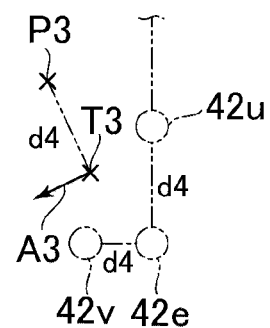
FIG. 9 is an explanatory diagram of one example of deciding an initial position of a node.

On the basis of the position of the tracker 12e indicated by the pose data acquired in the process illustrated in S101, the position T3 to which the right foot node 42e which is a target node is to move and a direction A3 toward which the right foot node 42e is to be oriented are identified, as illustrated in FIG. 9, for example. Then, a position P3 that is at a distance of a length d4 away, in a direction that is rotated at a predetermined angle (e.g., 90 degrees) from the left-right direction with respect to the direction A3, from the position T3 is decided as an initial position of the right calf node 42u which is the parent node 42 of the right foot node 42e. The length d4 here is the length of the bone 44t.

It is to be noted that a position obtained by interpolating the current position of the right calf node 42u and the position P3 may be decided as an initial position of the right calf node 42u, as in the abovementioned example.

Also, on the basis of the position of the tracker 12b indicated by the pose data acquired in the process illustrated in S101, a position to which the left hand node 42b which is a target node is to move and a direction toward which the left hand node 42b is to be oriented are identified, for example. Also, on the basis of the position of the tracker 12d indicated by the pose data acquired in the process illustrated in S101, a position to which the left foot node 42d which is a target node is to move and a direction toward which the left foot node 42d is to be oriented are similarly identified, for example. Also, initial positions of the remaining nodes 42 including the left forearm node 42m, the left calf node 42r, and the like are similarly decided.

Figure 10:
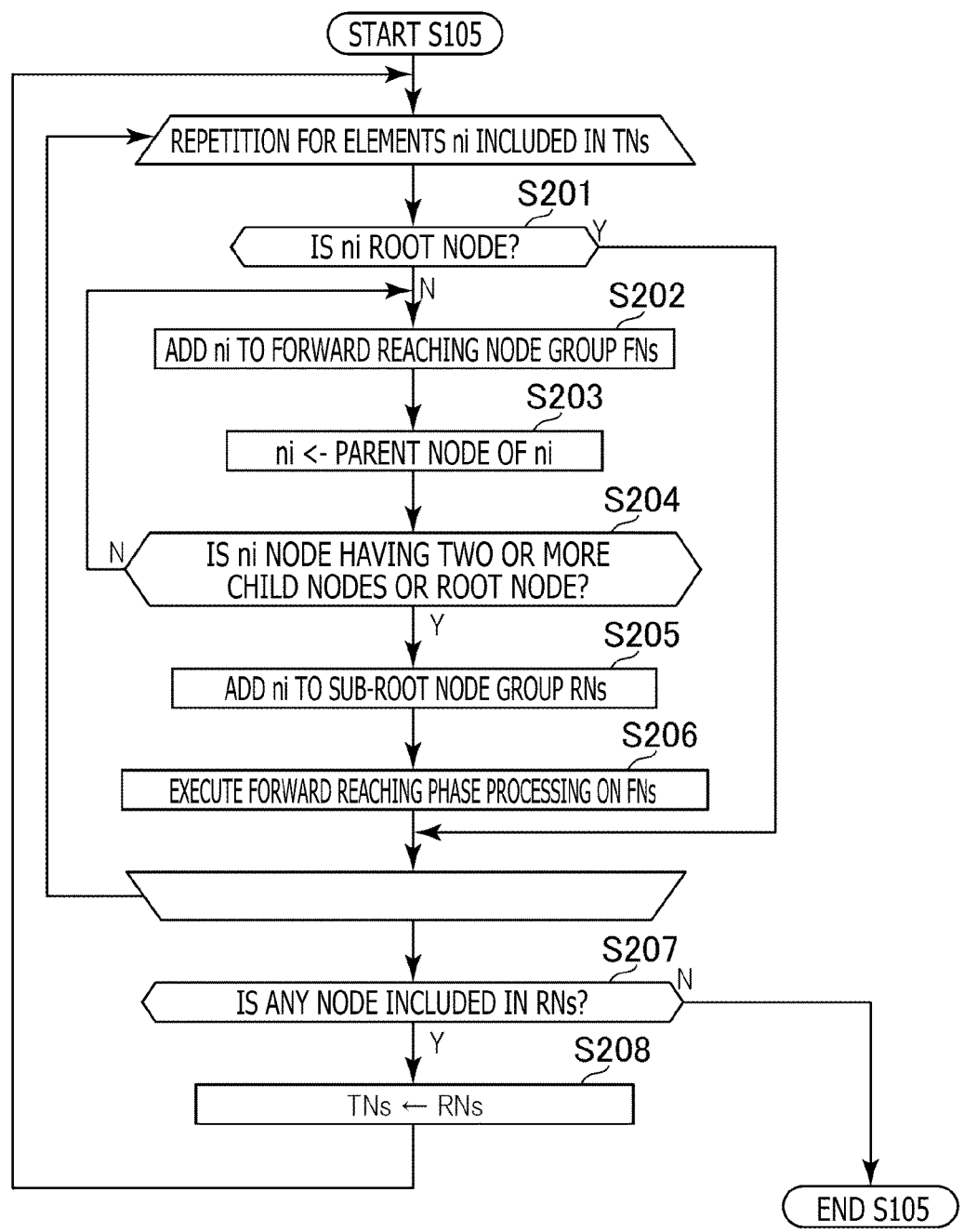
FIG. 10 is a flowchart illustrating one example of a process flow that is executed in an entertainment apparatus according to one embodiment of the present invention.

Subsequently, the pose updating section 56 executes the processes illustrated in S201 to S208 in FIG. 10 in which a list of the head node 42a, the left hand node 42b, the right hand node 42c, the left foot node 42d, and the right foot node 42e is used as an argument TNs (S105).

In the process illustrated in S105 using the list TNs of the nodes 42 as an argument, the processes illustrated in S201 to S206 which will be explained below are repeatedly executed on all elements ni included in TNs.

First, the pose updating section 56 determines whether or not ni is a root node (pelvis node 42f) (S201). In a case where ni is a root node (S201: Y), the loop of the processes illustrated in S201 to S206 is exited.

In a case where ni is not a root node (S201: N), the pose updating section 56 adds ni to a list FNs indicating a forward reaching node group of the present loop of the processes illustrated in S201 to S206 (S202).

Subsequently, the pose updating section 56 updates ni to a parent node 42 of ni (S203).

Then, the pose updating section 56 determines whether or not ni is a node 42 having two or more child nodes 42 or is the pelvis node 42f which is a root node (S204).

In a case where ni is neither a node 42 having two or more child nodes 42 nor a root node (S204: N), the process returns to the process illustrated in S202.

In a case where ni is a node 42 having two or more child nodes 42 or is a root node (S205: Y), the pose updating section 56 adds ni to a list RNs that indicates a sub-root node group (S205).

Subsequently, the pose updating section 56 executes the forward reaching phase processing of FABRIK, which has been explained with reference to FIG. 4, on the nodes 42 included in FNs (S206).

After the processes illustrated in S201 to S206 are executed on all the elements ni included in TNs, the pose updating section 56 determines whether or not any node 42 is included in the list RNs (S207).

In a case where any node 42 is included in the list RNs (S207: Y), the pose updating section 56 sets the list RNs as a list TNs in the next loop (S208). Then, the process returns to the process illustrated in S201. In this case, when the process illustrated in S202 is executed next time, ni is added to a new list FNs.

In a case where it is determined that no node 42 is included in the list RNs in S207 (S207: N), the process illustrated in S105 is ended.

According to the above process, five lists FNs each indicating a forward reaching node group are generated as a result of the first loop of the processes illustrated in S201 to S208 executed on the skeleton model 40 illustrated in FIG. 3. The first FNs includes the head node 42a and the neck node 42j, for example. The second FNs includes the left hand node 42b, the left forearm node 42m, the left upper arm node 42l, and the left collarbone node 42k, for example. The third FNs includes the right hand node 42c, the right forearm node 42p, the right upper arm node 42o, and the right collarbone node 42n, for example. The fourth FNs includes the left foot node 42d, the left calf node 42r, and the left thigh node 42q, for example. The fifth FNs includes the right foot node 42e, the right calf node 42u, and the right thigh node 42t, for example.

The list RNs indicating a sub-root node group of the first-time loop of the processes illustrated in S201 to S208 includes the pelvis node 42f which is a root node and the third spine node 42i. The abovementioned nodes 42 are disposed at nodal points in the skeleton model 40.

One list FNs indicating a forward reaching node group is generated by the second-time loop of the processes illustrated in S201 to S208. This list FNs includes the pelvis node 42f, the first spine node 42g, the second spine node 42h, and the third spine node 42i. As a result of the second-time loop of the processes illustrated in S201 to S208, the sub-root node group list RNs becomes empty.

Figure 11:
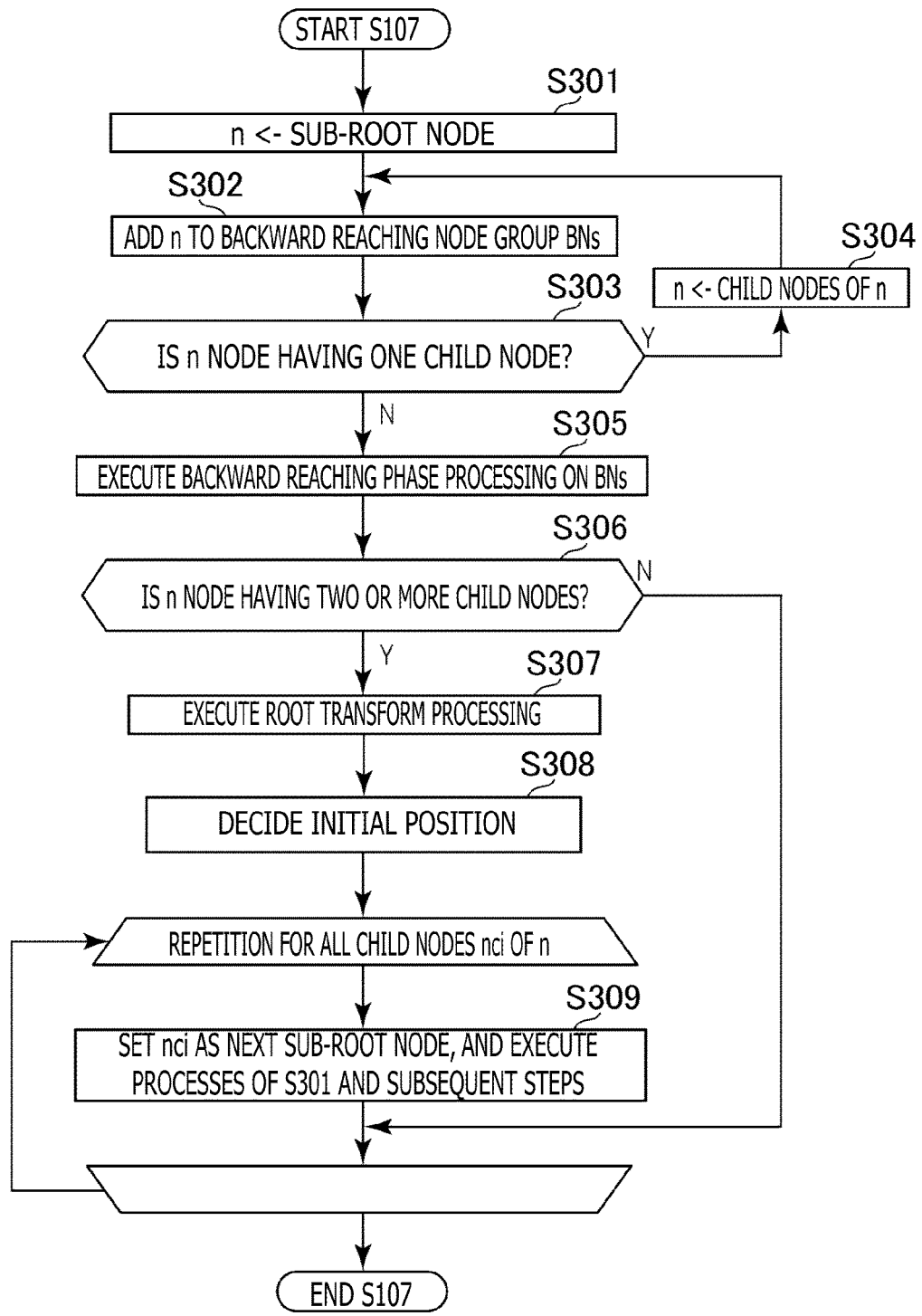
FIG. 11 is a flowchart illustrating one example of a process flow that is executed in an entertainment apparatus according to one embodiment of the present invention.

After the process illustrated in S105 is completed, the pose updating section 56 executes the processes illustrated in S301 to S309 depicted in FIG. 11 (S106).

In S106, the processes illustrated in S301 to S309 in which all the nodes 42 (sub-root nodes) included in the list RNs obtained by the first-time loop of the processes illustrated in S201 to S208 are used as arguments are executed. Here, in a case where two nodes 42 are included in RNs as explained above, the processes illustrated in S301 to S309 are executed two times. It is to be noted that the processes illustrated in S301 to S309 are executed on the nodes 42 having undergone the process illustrated in S105. Therefore, the processes illustrated in S301 to S309 are executed on the assumption that, for example, the left ball-of-foot node 42s and the right ball-of-foot node 42v are not included in the skeleton model 40.

First, the pose updating section 56 sets, as an element n, a sub-root node which is an argument (S301).

Next, the pose updating section 56 adds n to a list BNs that indicates a backward reaching node group (S302).

Subsequently, the pose updating section 56 determines whether or not n is a node 42 having one child node 42 (S303).

In a case where n is a node 42 having one child node 42 (S303: Y), the pose updating section 56 updates n to the child node 42 of n (S304). Then, the process returns to the process illustrated in S302.

In a case where n is not a node 42 having one child node 42 (S303: N), the pose updating section 56 executes the backward reaching phase processing of FABRIK, which has been explained with reference to FIG. 5, on the nodes 42 included in BNs (S305). It is to be noted that, here, in the case where the number of nodes 42 included in BNs is 1, execution of the backward reaching phase processing is skipped.

Subsequently, the pose updating section 56 determines whether or not n is a node 42 having two or more child nodes 42 (S306).

In a case where n is a node 42 having two or more child nodes 42 (S306: Y), the pose updating section 56 executes root transform processing (S307).

The root transform processing illustrated in S307 refers to updating the postures of some of the nodes 42 included in the skeleton model 40, for example. In a case where n is a node 42 having two or more child nodes 42, n is a node 42 at a nodal point included in the skeleton model 40. This updating may be executed such that the positions and the orientations of a plurality of nodes 42 including the node 42 at a nodal point match with the relative positions and orientations thereof in the standard pose, for example.

Here, for example, the postures of the third spine node 42i, the left collarbone node 42k, and the right collarbone node 42n may be updated with respect to the third spine node 42i. Here, for example, on the basis of the position of the left upper arm node 42l, rotation of the left upper arm node 42l about the bone 44c connecting the third spine node 42i and the second spine node 42h with respect to the standard pose may be identified. In addition, for example, on the basis of the position of the right upper arm node 42o, rotation of the right upper arm node 42o about the bone 44c with respect to the standard pose may be identified. On the basis of the two identified rotations, quaternion spherical linear interpolation may be executed to update the postures of the third spine node 42i, the left collarbone node 42k, and the right collarbone node 42n. Also, the postures of the pelvis node 42f, the left thigh node 42q, and the right thigh node 42t may be updated in a similar manner with respect to the pelvis node 42f.

Subsequently, the initial position deciding section 54 decides initial positions of some nodes 42 included in the skeleton model 40 (S308). It is assumed that, for example, the postures of the third spine node 42i, the left collarbone node 42k, and the right collarbone node 42n are updated in the process illustrated in S307. In this case, initial positions of the right upper arm node 42o, the left upper arm node 42l, the neck node 42j, and the second spine node 42h are decided on the basis of the updated postures of these nodes 42 and the standard pose of the skeleton model 40. Here, initial positions of the abovementioned nodes 42 may be decided such that the positions and the orientations thereof are adjusted with respect to the third spine node 42i which is a sub-root node in the standard pose, for example. In addition, it is assumed that, for example, the postures of the pelvis node 42f, the left thigh node 42q, and the right thigh node 42t are updated in the process illustrated in S307.

In this case, an initial position of the first spine node 42g may be decided on the basis of the updated postures of the abovementioned nodes 42 and the standard pose of the skeleton model 40. For example, the initial position of the first spine node 42g may be decided such that the position and the orientation thereof are adjusted with respect to the pelvis node 42f which is a sub-root node in the standard pose, for example.

Subsequently, on all elements nci which are the child nodes 42 of n, processes of S301 and subsequent steps in which nci is set as the next sub-root node are recursively and repeatedly executed (S309).

In a case where it is determined in S306 that n is not a node 42 having two or more child nodes 42 (S306: N), the process illustrated in S309 for the sub-root node is ended. That is, in a case where n is a node 42 disposed at an end in the skeleton model 40 subjected to the processes illustrated in S301 to S309, the process illustrated in S309 for the sub-root node is ended.

Then, when no element nci to be subjected to the process illustrated in S309 is left, the process illustrated in S106 is ended.

In the process illustrated in S106, the backward reaching phase processing is executed on the pelvis node 42f, the left thigh node 42q, the left calf node 42r, and the left foot node 42d, for example.

Further, the backward reaching phase processing is executed on the pelvis node 42f, the right thigh node 42t, the right calf node 42u, and the right foot node 42e.

Moreover, the backward reaching phase processing is executed on the pelvis node 42f, the first spine node 42g, the second spine node 42h, and the third spine node 42i.

In addition, the backward reaching phase processing is executed on the third spine node 42i, the neck node 42j, and the head node 42a.

In addition, the backward reaching phase processing is executed on the third spine node 42i, the left collarbone node 42k, the left upper arm node 42l, the left forearm node 42m, and the left hand node 42b.

In addition, the backward reaching phase processing is executed on the third spine node 42i, the right collarbone node 42n, the right upper arm node 42o, the right forearm node 42p, and the right hand node 42c.

After the process illustrated in S106 is completed, the pose updating section 56 determines whether or not a positional error at a target node is equal to or less than a predetermined threshold (S107). In this step, for example, whether or not the sum of distances each of which is between the position of each node 42 and a position to which the node 42 is to move and which is identified on the basis of the measurement results from the trackers 12 is equal to or less than the predetermined threshold is determined.

In a case where the positional error at the target node is not equal to or less than the predetermined threshold (S107: N), the pose updating section 56 executes steps the same as those in the process illustrated in S105 (S108). Subsequently, the pose updating section 56 executes steps the same as those in the process illustrated in S106 (S109). Then, the process returns to the process illustrated in S107. In the processes illustrated in S108 and S109, the above-mentioned lists may be reused.

In a case where it is determined in S107 that the positional error at the target node is equal to or less than the predetermined threshold (S107: Y), the pose updating section 56 updates the posture of a node 42 the posture of which is undecided (S110). It is to be noted that, in a case where the processes illustrated in S108 and S109 are executed a predetermined number of times, the process illustrated in S110 may be executed even if the positional error at the target node is not equal to or less than the predetermined threshold.

For example, the postures of the left ball-of-foot node 42s and the right ball-of-foot node 42v are updated in the process illustrated in S110. In this case, the updating may be executed such that the relative posture of the left ball-of-foot node 42s with respect to the posture of the left foot node 42d is identical to the relative posture in the standard pose. Further, the updating may be executed such that the relative posture of the right ball-of-foot node 42v with respect to the posture of the right foot node 42e is identical to the relative posture in the standard pose.

Subsequently, the pose updating section 56 updates the orientation of the bones 44 and rotation of the nodes 42 (S111). Then, the process returns to the process illustrated in S101. Subsequently, the processes illustrated in S101 to S111 are executed on the basis of pose data indicating new positions and new orientations of the trackers 12 acquired at the latest particular timing. In the manner explained so far, the processes illustrated in S101 to S111 are repeatedly executed.

Here, for example, the orientation of a bone 44 can be uniquely identified on the basis of the positions of the nodes 42 disposed at both ends of the bone 44. However, rotation about the bone 44 cannot be recognized from the positions of the nodes 42 disposed at both ends of the bone 44.

Figure 12:
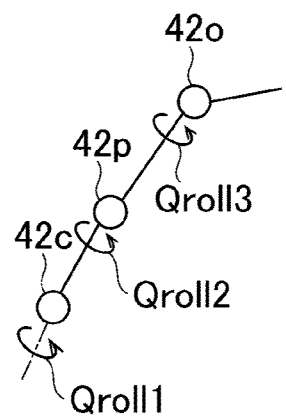
FIG. 12 is an explanatory diagram of one example of deciding rotation of a node.

Thus, in the process illustrated in S111, the pose updating section 56 divides rotation of the tracker 12b or the tracker 12c indicated by the pose data, into a component regarding bending of a wrist with respect to an arm, a component regarding rotation of an arm with respect to the standard pose, and a component regarding rotation about an arm, for example. In FIG. 12, a component regarding rotation of the right hand node 42c about a direction along the bone 44m is denoted by Qroll1.

Subsequently, the pose updating section 56 decides rotation of the upper arm and rotation of the forearm on the basis of the rotation about the arms. For example, components regarding rotation of the right hand node 42c about the bone 44m are decided as rotation Qroll2 of the right forearm node 42p about the arm and rotation Qroll3 of the right upper arm node 42o about the arm. Also, a component regarding rotation of the left hand node 42b about the bone 44i is decided as rotation of the left forearm node 42m about the arm and rotation of the left upper arm node 42l about the arm.

An upper limit of the difference between Qroll1 and Qroll2 or the difference between Qroll2 and Qroll3 may be preliminarily defined to 60 degrees, for example. In addition, a value obtained by multiplying the value of Qroll1 with a predetermined coefficient that is equal to or less than 1 may be set as the value of Qroll2. Also, a value obtained by multiplying the value of Qroll2 with a predetermined coefficient that is equal to or less than 1 may be set as the value of Qroll3.

As explained so far, in the present embodiment, the pose data acquiring section 52 acquires pose data indicating the posture of a target node included in the skeleton model 40 having a tree structure, in the process illustrated in S101, for example. Subsequently, the initial position deciding section 54 decides a position to which the target node is to move, on the basis of the pose data, in the process illustrated in S104. Further, in the process illustrated in S104, the initial position deciding section 54 decides an initial position of a parent node 42 of the target node for FABRIK calculation on the basis of the position to which the target node is to move and a given pose of the skeleton model 40. In addition, in the process illustrated in S308, the initial position deciding section 54 decides initial positions of some of the nodes 42 on the basis of the position to which the target node is to move and the given pose of the skeleton model 40.

In the above example, for example, a position that is at the distance d1 away, in a direction along the direction A2 but opposite to the direction A2, from the position T2 to which the right hand node 42c is to move, corresponds to a given posture in an initial position of the right forearm node 42p. In addition, for example, a position that is at the distance d4 away, in a direction that is rotated at a predetermined angle (e.g., 90 degrees) from the left-right direction with respect to the direction A3, from the position T3 corresponds to a given posture in an initial position of the right calf node 42u.

In addition, the given position and orientation with respect to a root node in the standard pose correspond to a given posture in the initial position of each of the right upper arm node 42o, the left upper arm node 42l, the neck node 42j, the second spine node 42h, and the first spine node 42g.

Moreover, in the processes illustrated in S105 to S111, the pose updating section 56 conducts the FABRIK calculation involving deciding a new position of a parent node 42 of a target node on the basis of a position to which the target node is to move and an initial position of the parent node 42. As a result, the pose of the skeleton model 40 is updated.

Thus, according to the present embodiment, a joint is not bent into an unnatural direction during pose decision using the FABRIK calculation, so that a possibility of an unreal pose of a human body lacking appropriateness being decided is reduced. As a result of this, the appropriateness of the result of decision of the pose of the skeleton model 40 can be improved.

In addition, in the process illustrated in S101 in the present embodiment, for example, the pose data acquiring section 52 acquires pose data indicating the posture of a target node included in the skeleton model 40 having a tree structure. Then, in the processes illustrated in S102 to S109, the pose updating section 56 updates the pose of the skeleton model 40 by conducting FABRIK calculation involving deciding a new position of a parent node 42 of the target node. Then, in the process illustrated in S111, the pose updating section 56 identifies rotation of the target node about the bone 44 connecting the target node and a parent node 42 of the target node, on the basis of the pose data. Then, in the process illustrated in S1/1, the pose updating section 56 decides rotation of the parent node 42 of the target node on the basis of the rotation of the target node.

Thus, according to the present embodiment, rotation about an arm can be decided on the basis of a measurement result obtained by each tracker 12. As a result, the appropriateness of the result of decision of the pose of the skeleton model 40 can be improved.

In addition, for example, in the process illustrated in S101 in the present embodiment, the pose data acquiring section 52 acquires pose data indicating postures of a plurality of nodes 42 including the posture of a first target node and posture of a second target node included in the skeleton model 40 having a tree structure.

Subsequently, in the process illustrated in S207, the pose updating section 56 conducts posture updating on a first group of nodes including the first target node and being connected to one another, on the basis of the pose data, by performing forward reaching phase processing of the FABRIK calculation. Further, similarly in the process illustrated in S207, the pose updating section 56 conducts posture updating on a second group of nodes including the second target node and being connected to one another, by performing forward reaching phase processing of the FABRIK calculation.

Subsequently, in the process illustrated in S307, the pose updating section 56 updates the postures of a plurality of the nodes 42 after updating the first node group and the second node group. For example, the plurality of nodes 42 here include a node 42 that is included in the first node group and is closest to a nodal point included in the skeleton model 40 and a node 42 that is included in the second node group and is closest to the nodal point included in the skeleton model 40.

Further, in the process illustrated in S304, the pose updating section 56 updates the pose of the skeleton model 40 through the backward reaching phase processing of the FABRIK calculation.

In this manner, the entire posture of a plurality of nodes 42 around a nodal point in the skeleton model 40 having a tree structure, such as the entire posture of a part ranging from the chest to the shoulders, that should not be largely distorted can be inhibited from being largely distorted in the present embodiment. As a result, the appropriateness of the result of decision of the pose of the skeleton model 40 can be improved.

In addition, in the process illustrated in S102 in the present embodiment, the pose updating section 46 may estimate a pivot foot on the basis of the pose data acquired in the process illustrated in S101.

Regarding a position indicated by the pose data, a coordinate value in a horizontal direction and a coordinate value in a height direction are referred to as a XY-coordinate value and a Z-coordinate value, respectively, in the following explanation. It is to be noted that the Z-coordinate value of a higher position is greater.

For example, the pose updating section 46 may compare the Z-coordinate value of the tracker 12d corresponding to the left foot and the Z-coordinate value of the tracker 12e corresponding to the right foot indicated by the pose data acquired in the process illustrated in S101.

Subsequently, in a case where the difference between the Z-coordinate values is greater than a predetermined value, the pose updating section 46 may presume a lower-side foot, that is, a foot having the smaller Z-coordinate value, to be a pivot foot. For example, in a case where the difference between the Z-coordinate values is greater than the predetermined value and the Z-coordinate value of the tracker 12d is smaller than the Z-coordinate value of the tracker 12e, the left foot may be presumed as a pivot foot. In contrast, in a case where the difference between the Z-coordinate values is greater than the predetermined value and the Z-coordinate value of the tracker 12e is smaller than the Z-coordinate value of the tracker 12d, the right foot may be presumed as a pivot foot.

Subsequently, the pose updating section 46 may decide an initial position of the pelvis node 42f (hip part node) for the FABRIK calculation on the basis of the position of the pivot foot.

For example, the pose updating section 46 may decide, as the XY-coordinate value of an initial position of the pelvis node 42f for the FABRIK calculation in the process illustrated in S102, an XY-coordinate value equal to the XY-coordinate value of the pivot foot.

In addition, in a case where the difference between the Z-coordinate values is less than the predetermined value, the pose updating section 46 may refrain from presuming either of the feet as a pivot foot. In this case, on an ellipse passing through the position of the tracker 12d and the position of the tracker 12e, for example, the pose updating section 46 may identify the XY-coordinate value of a position closest to a vertical line passing through the position of the tracker 12a indicated by the pose data acquired in the process illustrated in S101.

The identified XY-coordinate value may be decided as the XY-coordinate value of an initial position of the pelvis node 42*f* for the FABRIK calculation in the process illustrated in S102. The distance between the position of the tracker 12*d* and the position of the tracker 12*e* may be adopted as the length in the longer axis direction of this ellipse, and a predetermined length may be adopted as the length in the shorter axis direction of this ellipse.

In addition, an XY-coordinate value obtained by linearly interpolating an XY-coordinate value equal to the XY-coordinate value of the pivot foot and the XY-coordinate value of the abovementioned position on the ellipse passing through the position of the tracker 12*d* and the position of the tracker 12*e* may be decided as the XY-coordinate value of an initial position of the pelvis node 42*f*.

A weight in the linear interpolation may be decided on the basis of the difference between the Z-coordinate value of the tracker 12*d* and the Z-coordinate value of the tracker 12*e*, for example. For example, an XY-coordinate value that becomes closer to the XY-coordinate value of the abovementioned position on the ellipse when the difference between the Z-coordinate values is smaller may be decided as the XY-coordinate value of the initial position of the pelvis node 42*f*. Also, an XY-coordinate value that becomes closer to an XY-coordinate value equal to the XY-coordinate value of the pivot foot when the difference between the Z-coordinate values is larger may be decided as the XY-coordinate value of the initial position of the pelvis node 42*f*.

Further, the pose updating section 46 may correct the XY-coordinate value of the initial position of the pelvis node 42*f* that is decided as described above, on the basis of the position of the tracker 12*a* indicated by the pose data acquired in the process illustrated in S101. For example, the XY-coordinate value of the initial position of the pelvis node 42*f* may be corrected such that the initial position of the pelvis node 42*f* is shifted, along a horizontal plane, toward a direction opposite to a direction extended from the pivot foot or the center point between the two feet to the position of the tracker 12*a*. For example, the XY-coordinate value of the initial position of the pelvis node 42*f* may be corrected such that, in a case where the position of the tracker 12*a* is forward of the pivot foot or the center point between the two feet, the initial position of the pelvis node 42*f* is shifted backward. In addition, the XY-coordinate value of the initial position of the pelvis node 42*f* may be corrected such that, in a case where the position of the tracker 12*a* is backward of the pivot foot or the center point between the two feet, the initial position of the pelvis node 42*f* is shifted frontward.

On the basis of the position and the orientation of the tracker 12*a*, the Z-coordinate values of initial positions of the bone 44*e*, the bone 44*d*, the bone 44*c*, the bone 44*b*, and the bone 44*a* and the initial position of the pelvis node 42*f* for the FABRIK calculation may be decided.

In addition, in the present embodiment, the pose updating section 46 may estimate whether the user is in a sitting position or a standing position by using a machine learning model that has been learned, in the following manner. Further, in a case where the user is estimated to be in a standing position, a pivot foot may be presumed and an initial position of the pelvis node 42*f* (hip part node) for the FABRIK calculation may be decided on the basis of the pivot-foot estimation result, in the abovementioned manner.

Figure 13:
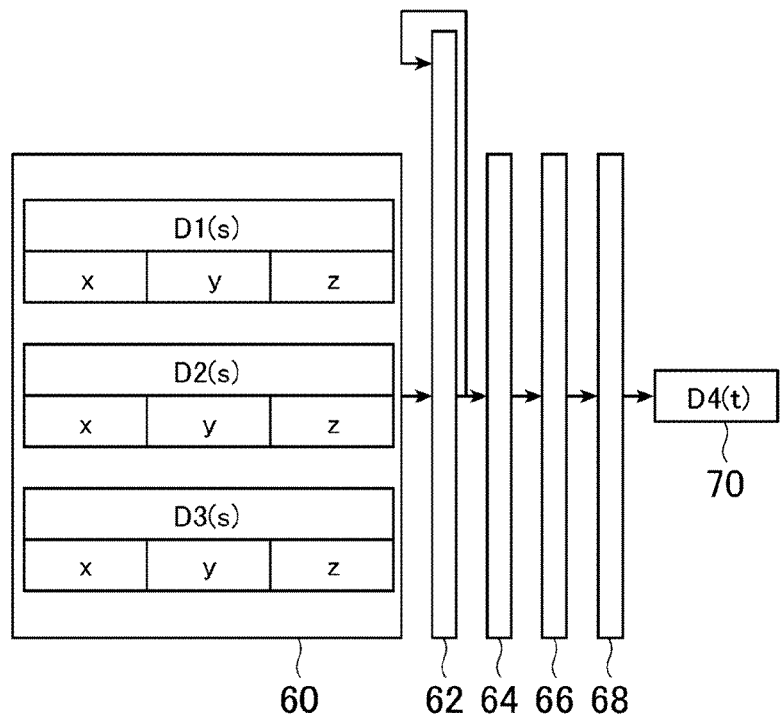
FIG. 13 is a diagram illustrating one example of learning of a machine learning model that is used to estimate whether a user is in a sitting position or a standing position.

FIG. 13 is a diagram illustrating one example of learning of a machine learning model that is used to estimate whether a user is in a sitting position or a standing position. As illustrated in FIG. 13, the machine learning model that is used to estimate whether a user is in a sitting position or a standing position includes an input layer 60, an intermediate block 62, a first intermediate layer 64, a second intermediate layer 66, and an output layer 63.

In the present embodiment, by learning of the machine learning model illustrated in FIG. 13, learning data including a plurality of part data sets that are associated with different timings, and that each indicate the orientation of the head part offset by rotation of the hip part (pelvis node 42*f*) (with respect to the orientation of the hip part), the position of the head with respect to the position of the right foot, and the position of the head with respect to the position of the left foot at each timing is acquired, for example.

Here, for example, when a user with the trackers 12 respectively mounted on the head part, the right foot, the left foot, and the hip part, for example, is making a variety of motions while being in a sitting position, sensing data is outputted from the trackers 12. On the basis of the sensing data, a series of part data sets corresponding to the sitting position may be generated. Alternatively, for example, on the basis of a video of the user who is making a variety of motions while being in a sitting position, the video being captured by an external camera, a series of part data sets corresponding to the sitting position may be generated. Alternatively, according to an operation performed by an operator who is watching the video, a series of part data sets corresponding to the sitting position may be generated.

Then, for example, learning data including the series of part data sets corresponding to the sitting position and teacher data having a value set to 1 may be generated.

Further, for example, when the user with the trackers 12 respectively mounted on the head part, the right foot, the left foot, and the hip part is making a variety of motions while being in a standing position, sensing data is outputted from the trackers 12. On the basis of the sensing data, a series of part data sets corresponding to the standing position may be generated. Alternatively, for example, on the basis of a video including t frames obtained by capturing, by means of an external camera, an image of the user who is making a variety of motions while being in a standing position, a series of part data sets corresponding to the standing position may be generated. Alternatively, according to an operation performed by an operator who is watching the video, a series of part data sets corresponding to the standing position may be generated.

Then, learning data including the abovementioned series of part data sets corresponding to the standing position and teacher data having a value set to 1 may be generated.

Then, the part data sets included in the learning data are sequentially inputted to the input layer 60 in order from the part data set associated with the oldest timing. For example, it is assumed here that the part data sets include head orientation data D1 indicating the orientation of the head part offset by rotation of the hip part, right foot-based head position data D2 indicating the position of the head part with respect to the position of the right foot and having been offset by rotation of the hip part, and left foot-based head position data D3 indicating the position of the head part with respect to the position of the left foot and having been offset by rotation of the hip part.

For example, here, head orientation data associated with the s-th oldest timing is denoted by $D1(s)$. Further, right foot-based head position data associated with the s-th oldest timing is denoted by $D2(s)$. Further, left foot-based head position data associated with the s-th oldest timing is denoted by $D3(s)$. Here, the value of s is an integer of 1 to t.

In addition, in the present embodiment, the head orientation data $D1(s)$ includes three elements such as x, y, and z, as illustrated in FIG. 13. The three elements respectively correspond to the x-coordinate value, the y-coordinate value, and the z-coordinate value of a vector having been offset by rotation of the chest part and indicating the orientation of the head part. For example, the vector having been offset by rotation of the chest part and indicating the orientation of the head part may be a unit vector indicating the orientation (e.g., the visual direction of the head part) of the head part (the head node 42a) offset by rotation of the chest part. It is to be noted that the vector having been offset by rotation of the chest part and indicating the orientation of the head part may be a vector indicating the position of the head part (the head node 42a) with respect to the position of the neck (the neck node 42j). In this case, each part data set included in the learning data may be generated on the basis of sensing data that is outputted from the trackers 12 when a user having the trackers 12 respectively mounted on the head part, the right foot, the left foot, the hip part, and the neck makes a variety of motions.

In addition, in the present embodiment, the right foot-based head position data D2(s) includes three elements such as x, y, and z, as illustrated in FIG. 13. The three elements respectively correspond to the x-coordinate value, the y-coordinate value, and the z-coordinate value of the position of the head part with respect to the position of the right foot, the position being offset by rotation of the hip part.

In addition, in the present embodiment, the left foot-based head position data D3(s) includes three elements such as x, y, and z, as illustrated in FIG. 13. The three elements respectively correspond to the x-coordinate value, the y-coordinate value, and the z-coordinate value of the position of the head part with respect to the position of the left foot, the position being offset by rotation of the hip part.

In the present embodiment, part data including nine (3×3) elements is inputted to the input layer 60.

Then, input data obtained by combining the part data inputted to the input layer 60 with output from the intermediate block 62 in response to the last input is inputted to the intermediate block 62. In the present embodiment, the intermediate block 62 is an RNN (Recurrent Neural Network) (LSTM block) having an LSTM (Long short-term memory) installed therein, for example.

Here, the output from the intermediate block 62 is data indicating a time-series feature of the position, the posture, or a motion of a body part indicated by the part data. Hereinafter, data that is outputted from the intermediate block 62 is referred to as feature data. For example, a state variable of the LSTM corresponds to the feature data.

For example, it is assumed here that input data including part data associated with a certain timing and feature data indicating a time-series feature obtained up to the timing is inputted to the intermediate block 62. In this case, the intermediate block 62 outputs the feature data indicating the time-series feature obtained up to the timing. For example, it is assumed that input data including the (s−1)-th part data and the feature data indicating the time-series feature obtained up to a timing corresponding to the (s−1)-th part data is inputted to the intermediate block 62. In this case, the intermediate block 62 outputs the feature data indicating the time-series feature obtained up to the timing corresponding to the s-th part data. Hereinafter, the feature data indicating the time-series feature obtained up to the timing corresponding to the s-th part data is referred to as s-th feature data.

Then, the t-th feature data, which is outputted from the intermediate block 62 in response to input of input data including the last part data (t-th part data), is inputted to the first intermediate layer 64. Subsequently, output from the first intermediate layer 64 is inputted to the second intermediate layer 66. Each of the first intermediate layer 64 and the second intermediate layer 66 is a fully connected layer adopting a rectified linear unit (ReLU) as an activation function, for example.

Then, output from the second intermediate layer 66 is inputted to the output layer 68. The output layer 68 is a layer adopting a rectified linear unit as an activation function, for example. Then, sitting probability data D4(t) that corresponds to an estimation result as to whether the user is in a sitting position or a standing position at the latest timing (t-th timing) is outputted as output 70 from the output layer 68. The sitting probability data is expressed by a real number of 0 to 1, for example. The higher value of the sitting probability data indicates that the probability that the user is in a sitting position is higher, while the lower value of the sitting probability data indicates that the probability that the user is in a sitting position is lower.

Then, in the present embodiment, learning in the intermediate block 62, the first intermediate layer 64, the second intermediate layer 66, and the output layer 68 is conducted on the basis of the sitting probability data D4(t) which indicates the estimation result, for example. Here, the difference between the teacher data included in the learning data including the abovementioned series of part data sets and the sitting probability data D4(t) indicating the estimation result may be identified. On the basis of the identified difference, supervised leaning in which the values of parameters in the intermediate block 62, the first intermediate layer 64, the second intermediate layer 66, and the output layer 68 are updated may be conducted.

In the present embodiment, learning is conducted using learning data including t part data sets consisting of the first part data to the t-th part data, for example. Here, learning may be conducted using learning data including t part data sets consisting of the first part data to the t-th part data and the abovementioned teacher data associated with the t part data sets, for example. Then, for example, learning using a plurality of different learning data sets corresponding to the sitting position and a plurality of different learning data sets corresponding to the standing position is conducted to obtain a learned machine learning model, and the leaned machine learning model is used to estimate whether the user is in a sitting position or a standing position.

Figure 14:
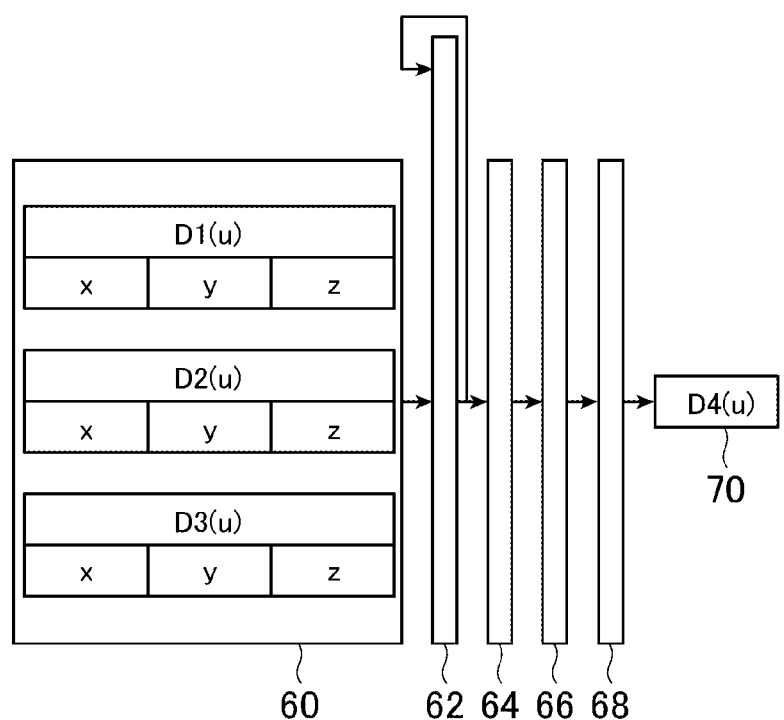
FIG. 14 is a diagram illustrating one example of estimating whether a user is in a sitting position or a standing position by using the machine learning model that has been learned as illustrated in FIG. 13.

FIG. 14 is a diagram illustrating one example of estimating whether a user is in a sitting position or a standing position by using a machine learning model that has been learned.

As previously explained, in the present embodiment, the position and the orientation of each of the trackers 12a to 12e are identified at a predetermined sampling rate, for example. According to the identification of the positions and the orientations of the trackers 12, data indicating the positions and the orientations of the trackers 12 is transmitted to the entertainment apparatus 14.

On the basis of the data indicating the positions and the orientations of the trackers 12 transmitted in the abovementioned manner, the abovementioned part data sets are generated. In this manner, the part data sets are repeatedly generated, for example, in the present embodiment.

It is assumed here that a part data set includes the head orientation data D1 having been offset by rotation of the hip part and indicating the orientation of the head part, the right foot-based head position data D2 having been offset by rotation of the hip part and indicating the position of the head part with respect to the position of the right foot, and the left foot-based head position data D3 having been offset by rotation of the hip part and indicating the position of the head part with respect to the position of the left foot, as previously explained. It is to be noted that, in a case where the head orientation data D1 is a vector indicating the position of the head part (head node 42a) with respect to the position of the neck (neck node 42j), the head orientation data D1 may be generated on the basis of the latest positions of the neck node 42j and the head node 42a.

Then, in the present embodiment, the latest part data (part data that is generated last) is inputted to the input layer 60, for example. In FIG. 14, the head orientation data included in the latest part data is denoted by D1(u). In addition, the right foot-based head position data included in the latest part data is denoted by D2(u). In addition, the left foot-based head position data included in the latest part data is denoted by D3(u).

As previously explained, the head orientation data D1(u) includes three elements such as x, y, and z. Also, the right foot-based head position data D2(u) includes three elements such as x, y, and z. Also, the left foot-based head position data D3(u) includes three elements such as x, y, and z.

Further, input data obtained by combining the part data including 9 (3×3) elements and having been inputted to the input layer 60 with feature data having been outputted from the intermediate block 62 in response to the last input is inputted to the intermediate block 62.

Then, the feature data which is output from the intermediate block 62 is inputted to the first intermediate layer 64. Then, output from the first intermediate layer 64 is inputted to the second intermediate layer 66.

Subsequently, output from the second intermediate layer 66 is inputted to the output layer 68. Then, the sitting probability data D4(u) which corresponds to an estimation result as to whether the user is in a sitting position or a standing position at the timing is outputted as the output 70 from the output layer 68.

Here, for example, in a case where the value of the sitting probability data D4(u) is equal to or greater than 0.5, it may be estimated that the user is in a sitting position. Otherwise, it may be estimated that the user is in a standing position.

In a case where it is estimated that the user is in a standing position, the pivot foot may be estimated, and an initial position of the pelvis node 42f may be decided on the basis of the pivot foot estimation result, in the abovementioned manner.

It is to be noted that it is not necessary to estimate whether the user is in a sitting position or a standing position by using a machine learning model. For example, any given logic created may be used to estimate whether the user is in a sitting position or a standing position.

In addition, as the value of the right foot-based head position data D2 or the value of the left foot-based head position data D3, a relative value with respect to the body size, that is, a value obtained by dividing a coordinate value of the head position with respect to the foot position, by the body size, may be used.

Here, the body size may be preliminarily inputted by the user, or may be sequentially estimated on the basis of the positions of the trackers 12 each time whether the user is in a sitting position or a standing position is estimated, for example.

Figure 15:
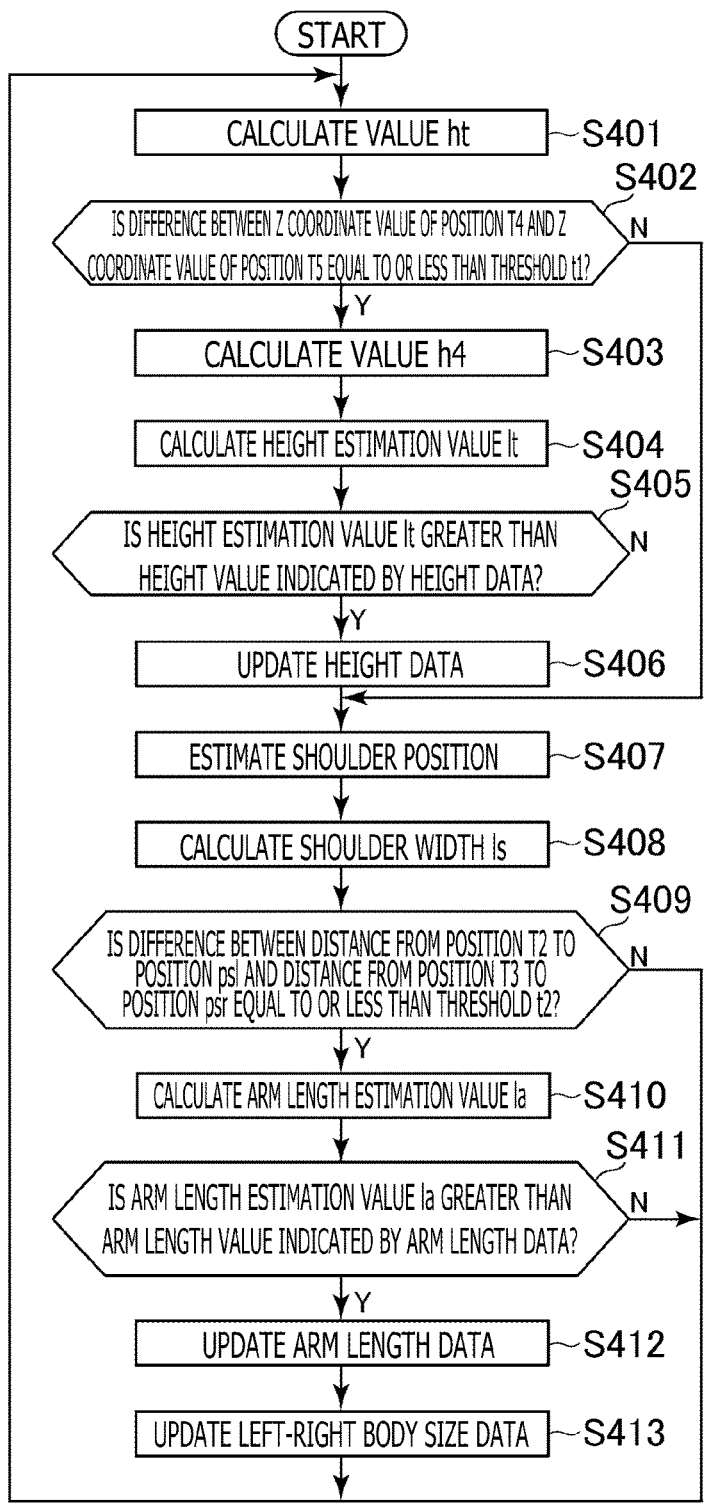
FIG. 15 is a flowchart illustrating one example of a process flow that is executed in an entertainment apparatus according to one embodiment of the present invention.
Figure 16:
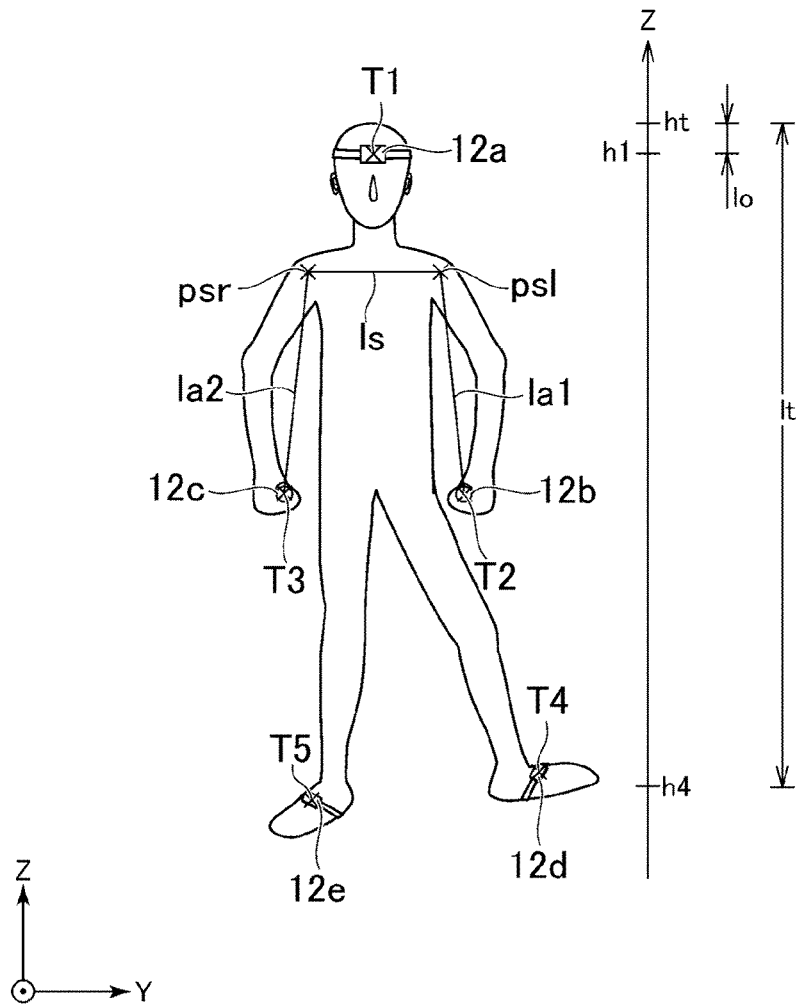
FIG. 16 is a schematic diagram illustrating one example in which a user is playing a game.

Here, one example of a body size estimating process flow which is executed in the entertainment apparatus 14 according to the present embodiment will be explained with reference to a flowchart in FIG. 15 and a schematic diagram in FIG. 16. FIG. 16 is a schematic diagram illustrating one example in which a user is playing a game. In the present process example, the processes illustrated in S401 to S413 are repeatedly executed at a predetermined sampling rate. The processes of the present process example may be executed immediately before the abovementioned pivot foot estimating process is executed, for example. Further, in the following explanation, the front-rear direction, the left-right direction, and the height direction of the user are defined as an X-axis direction, a Y-axis direction, and a Z-axis direction, respectively.

Further, in the following explanation, the positions of the tracker 12a, the tracker 12b, the tracker 12c, the tracker 12d, and the tracker 12e indicated by the pose data acquired in the process illustrated in S101 are denoted by T1, T2, T3, T4, and T5, respectively, as illustrated in FIG. 16.

In addition, in the following explanation, it is assumed that body size data indicating the body size of the user is stored in the skeleton model data storage section 50. A predetermined value is defined here as an initial value of the body size data, for example. Alternatively, a value according to the age of the user may be defined as an initial value of the body size data. The body size indicated by the body size data is updated to be gradually increased, as explained later. Therefore, it is desirable to define, as the initial value of the body size data, a value that is slightly less than a value indicating a typical user body size.

It is to be noted that the skeleton model data storage section 50 may store height data indicating the height of the user. In addition, the skeleton model data storage section 50 may store arm length data indicating the length of a user's arm. In addition, the skeleton model data storage section 50 may store left-right body size data indicating the size of the user's body in the left-right direction.

First, the pose updating section 56 calculates, as a Z-coordinate value ht of the crown part, a value obtained by adding a predetermined offset value lo to the Z-coordinate value hi of the position T1 (S401).

Subsequently, the pose updating section 56 determines whether or not the difference between the Z-coordinate value of the position T4 and the Z-coordinate value of the position T5 is equal to or less than a predetermined threshold t1 (S402).

In a case where it is determined that the difference between the Z-coordinate value of the position T4 and the Z-coordinate value of the position T5 is equal to or less than the threshold t1 (S402: Y), the pose updating section 56 calculates a Z-coordinate value h4 which is an average value of the Z-coordinate value of the position T4 and the Z-coordinate value of the position T5 (S403).

Next, the pose updating section 56 calculates, as an estimated height value lt, the difference between the Z-coordinate value ht of the crown part calculated in the process illustrated in S401 and the Z-coordinate value h4 calculated in the process illustrated in S403 (S404).

Subsequently, the pose updating section 56 determines whether or not the estimated value it of the body size calculated in the process illustrated in S404 is greater than a height value indicated by the height data stored in the skeleton model data storage section 50 (S405).

In a case where it is determined that the value lt is greater than the height value indicated by the height data stored in the skeleton model data storage section 50 (S405: Y), the pose updating section 56 updates the height data stored in the skeleton model data storage section 50, to indicate the estimated value lt of the body size calculated in the process illustrated in S404 (S406).

Subsequently, the pose updating section 56 estimates the positions of the user's shoulders (S407). Here, for example, a predetermined offset value psro may be added to the value indicating the position T1 such that a value indicating the position psr of the right shoulder can be estimated. In addition, for example, another predetermined offset value pslo may be added to the value indicating the position T1 such that a value indicating the position psl of the left shoulder can be estimated. It is to be noted that, also in a case where it is determined in the process illustrated in S403 that the difference between the Z-coordinate value of the position T4 and the Z-coordinate value of the position T5 is not equal to or less than the threshold t1 (S402: N), the process illustrated in S407 is executed. In this case, it is highly likely that the value indicating the position T4 or the value indicating the position T5 is an abnormal value based on an error. Thus, the processes illustrated in S403 to S406 are skipped. Further, also in a case where it is determined in the process illustrated in S405 that the value lt is not greater than the height value indicated by the height data stored in the skeleton model data storage section 50 (S405: N), the process illustrated in S407 is executed.

Subsequently, the pose updating section 56 calculates, as a shoulder width ls, the distance between the position psr of the right shoulder and the position psi of the left shoulder estimated in the process illustrated in S407 (S408).

Subsequently, the pose updating section 56 determines whether or not the difference between the distance from the position T2 to the position psl and the distance from the position T3 to the position psr is equal to or less than a predetermined threshold t2 (S409).

In a case where it is determined that the difference between a distance la1 from the position T2 to the position psl and a distance la2 from the position T3 to the position psr is equal to or less than the predetermined threshold t2 (S409: Y), the pose updating section 56 calculates, as an estimated arm length value la, the average value of a value indicating the distance la1 from the position T2 to the position psr and a value indicating the distance la2 from the position T3 to the position psl (S410).

Subsequently, the pose updating section 56 determines whether or not the estimated value la calculated in the process illustrated in S410 is greater than an arm length value indicated by arm length data stored in the skeleton model data storage section 50 (S411).

In a case where it is determined that the value la is greater than the value of the arm length data stored in the skeleton model data storage section 50 (S411: Y), the pose updating section 56 updates the arm length data stored in the skeleton model data storage section 50, to indicate the estimated arm length value la calculated in the process illustrated in S410 (S412).

Subsequently, the pose updating section 56 updates the left-right body size data stored in the skeleton model data storage section 50, to indicate the sum of the doubled value of the arm length data and the value of the abovementioned shoulder width ls (S413). Thereafter, the process returns to the process illustrated in S401.

It is to be noted that, also in a case where it is determined in the process illustrated in S409 that the difference between the distance from the position T2 to the position psl and the distance from the position T3 to the position psr is not equal to or less than the predetermined threshold t2 (S409: N), the process returns to the process illustrated in S401. In this case, it is highly likely that the value indicating the position T2 or the value indicating the position T3 is an error-based abnormal value. Thus, the processes illustrated in S410 to S413 are skipped. Further, also in a case where it is determined in the process illustrated in S411 that the value la is not greater than the arm length value indicated by the arm length data stored in the skeleton model data storage section 50 (S411: N), the process returns to the process illustrated in S401.

For example, a value obtained by dividing a coordinate value of the head position with respect to the foot position, by the value of the height size data, the value of the arm length data, or the value of the left-right body size data stored in the skeleton model data storage section 50, may be used as each of the value of the right foot-based head position data D2 or the value of the left foot-based head position data D3.

In addition, also during learning of the machine learning model illustrated in FIG. 13, the processes in S401 to S413 may be executed. Then, a value obtained by dividing a coordinate value of the head position with respect to the foot position, by the value of the height size data, the value of the arm length data, or the value of the left-right body size data, may be used as each of the value of the right foot-based head position data D2 and the value of left foot-based head position data D3.

It is to be noted that, in place of the skeleton model 40 in an A-pose, the skeleton model 40 in what is generally called a T-pose with the legs apart and the arms extended in the horizontal direction may be used as the skeleton model 40 in a standard pose, in the explanation below.

In the present embodiment, body tracking using a non-human skeleton model 40 modeling a dog, a dragon, an octopus, or the like is demanded in some cases.

Figure 17:
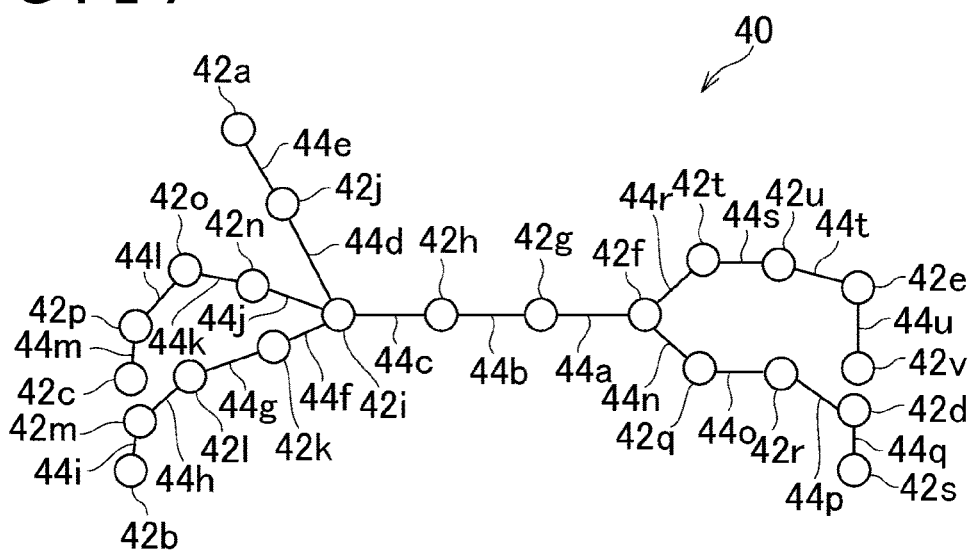
FIG. 17 is a diagram illustrating one example of a default pose of a skeleton model.

FIG. 17 illustrates the skeleton model 40 modeling a four-legged dog as one example of the non-human skeleton model 40.

As illustrated in FIG. 17, a default pose of a certain skeleton model 40 is not set to a known standard pose such as a T-pose or an A-pose. To perform the body tracking according to the present embodiment by using this type of the skeleton model 40, the skeleton model 40 the pose of which has been changed to a known standard pose needs to be prepared, as previously explained.

Figure 18:
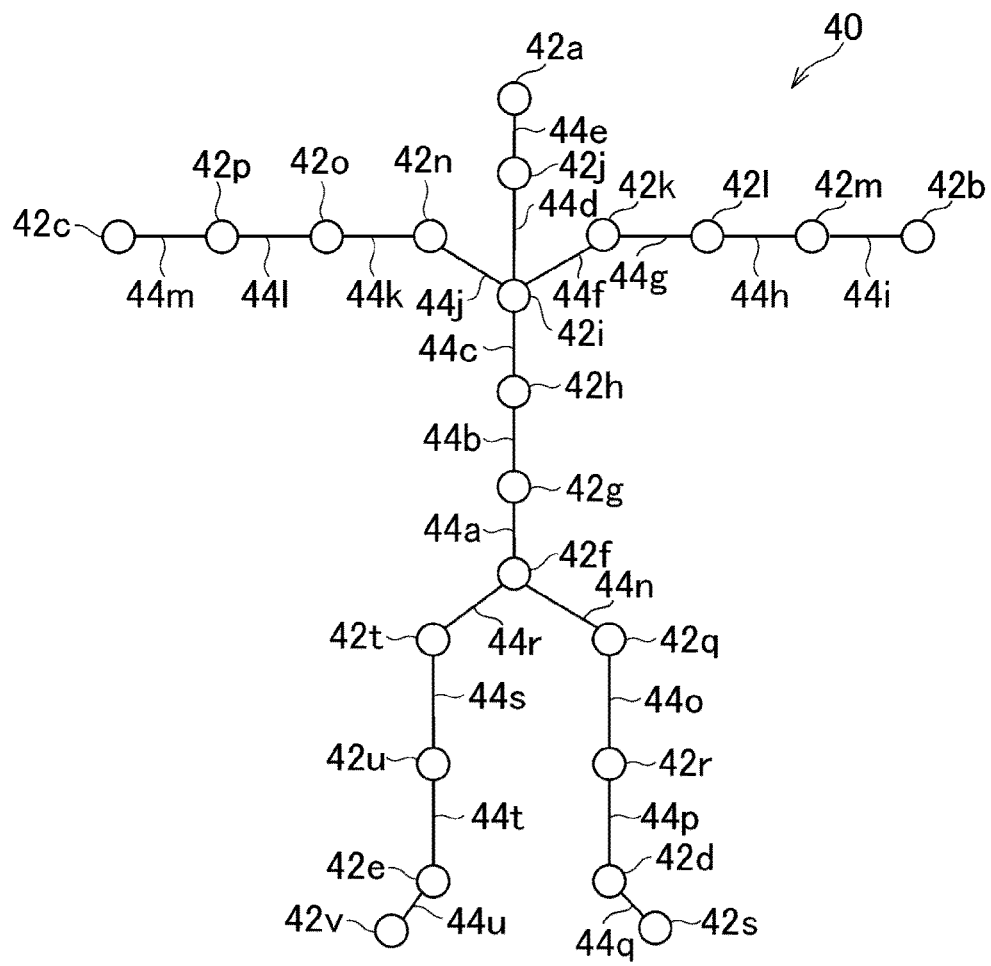
FIG. 18 is a diagram illustrating one example of a skeleton model the pose of which has been changed to a T-pose.

FIG. 18 is a diagram illustrating one example in which the pose of the skeleton model 40 illustrated in FIG. 17 is changed to a T-pose which is one of known standard poses.

Here, if a worker manually changes the pose of the skeleton model 40 illustrated in FIG. 17 to the standard pose illustrated in FIG. 18, a lot of time and effort of the worker are required. As such, in the present embodiment, time and effort for changing the pose of the skeleton model 40 to a known standard pose can be reduced, as follows.

Hereinafter, the functions of the entertainment apparatus 14 according to the present embodiment and processes which are executed in the entertainment apparatus 14 according to the present embodiment that are related to a change of the skeleton model 40 to a T-pose will be explained in more detail.

Figure 19:
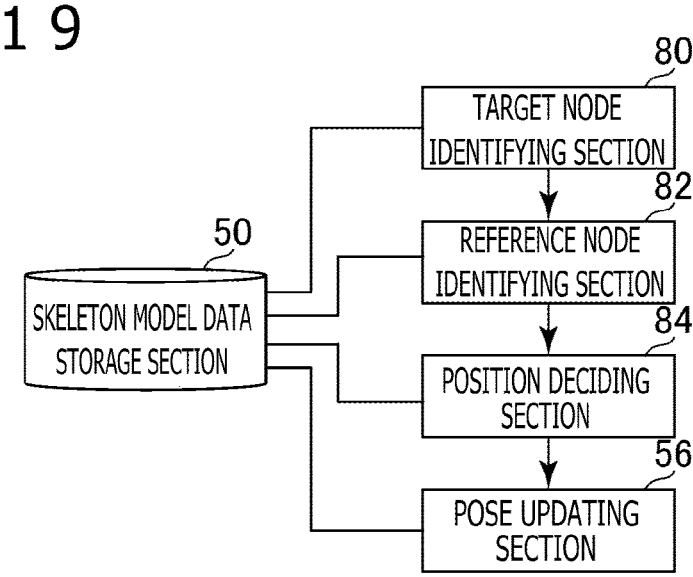
FIG. 19 is a functional block diagram illustrating one example of functions that are implemented by an entertainment apparatus according to one embodiment of the present invention.

FIG. 19 is a functional block diagram illustrating examples of the functions of the entertainment apparatus 14 according to the present embodiment, related to a change of the skeleton model 40 to a T-pose. It is to be noted that all the functions illustrated in FIG. 19 are not necessarily required to be implemented by the entertainment apparatus 14 according to the present embodiment, and any function other than those illustrated in FIG. 19 may be implemented.

As illustrated in FIG. 19, the entertainment apparatus 14 according to the present embodiment functionally includes the skeleton model data storage section 50, the pose updating section 56, a target node identifying section 80, a reference node identifying section 82, and a position deciding section 34, for example.

The skeleton model data storage section 50 is implemented mainly by the storage section 32. The pose updating section 56, the target node identifying section 80, the reference node identifying section 82, and the position deciding section 84 are implemented mainly by the processor 30.

These functions may be implemented when the processor 30 executes a program that has been installed in the entertainment apparatus 14, which is a computer, and that includes commands corresponding to the functions. This program may be supplied to the entertainment apparatus 14 via a computer-readable information recording medium such as an optical disk, a magnetic disk, a magnetic tape, a magneto-optical disk, or a flash memory, or over the internet or the like.

In the present embodiment, the skeleton model data storage section 50 stores skeleton model data indicating the pose of the skeleton model 40, for example, as previously explained. Here, it is assumed that, for example, skeleton data indicating the pose of the skeleton model 40 that is not in a known standard pose, as illustrated in FIG. 17, is preliminarily stored in the skeleton model data storage section 50.

In the present embodiment, the target node identifying section 80 identifies a plurality of target nodes from among a plurality of nodes included in the skeleton model 40 being in a pose other than the known standard pose, for example. Here, a user may be allowed to perform operation input to the entertainment apparatus 14 through a controller that is communicable with the entertainment apparatus 14, for example. According to a target node selecting operation by the user, the target node identifying section 80 may identify, as the target nodes, nodes selected by the user.

Here, it is assumed that nodes (the head node 42a, the left hand node 42b, the right hand node 42c, the left foot node 42d, and the right foot node 42e) that are linked with the trackers 12 in body tracking are identified as the target nodes, for example. It is to be noted that, here, nodes at ends may be identified as target nodes. In addition, in a case where the nodes 42 are associated with corresponding names, the target node identifying section 80 may identify the target nodes on the basis of the names of the nodes 42.

Further, among nodes of three branches, nodes at ends distant from the node positioned at the branch point by the same number of nodes may be identified as a target node corresponding to the right hand and a target node corresponding to the left hand. Further, a node at the remaining one end may be identified as a target node corresponding to the head part.

Further, among nodes of two branches, nodes at the ends may be identified as a target node corresponding to the right foot and a target node corresponding to the left node, respectively.

In addition, in a case where the skeleton model 40 includes a tail node, there may be two sets of three branches of nodes. In this case, nodes corresponding to the head part, the left hand, the right hand, the right foot, the left foot, and the tail may be identified on the basis of the relative positions (up/down, left/right, front/rear) of the nodes at the respective ends.

In the present embodiment, the reference node identifying section 82 identifies a reference node that is disposed closest to the side of the target nodes, from among nodes connected to all of the plurality of target nodes via one or more bones, for example. Here, the pelvis node 42f is identified as a reference node for the left foot node 42d and the right foot node 42e, for example. Further, the third spine node 42i is identified as a reference node for the head node 42a, the left hand node 42b, and the right hand node 42c.

In the present embodiment, the position deciding section 84 decides the position of the reference node and the positions of the target nodes, for example. The position deciding section 84 decides the position of the reference node and the positions of the plurality of target nodes such that relative positions of the plurality of target nodes with respect to the position of the reference node are adjusted to predetermined positions.

In the present embodiment, the pose updating section 56 updates the pose of the skeleton model 40 to the known standard pose on the basis of the positions of the plurality of target nodes decided by the position deciding section 84, for example. The pose updating section 56 updates the pose of the skeleton model 40 to the known standard pose by executing the processes in S105 to S111, for example. Here, the pose of the skeleton model 40 is updated to a T-pose, as illustrated in FIG. 18, for example.

Figure 20:
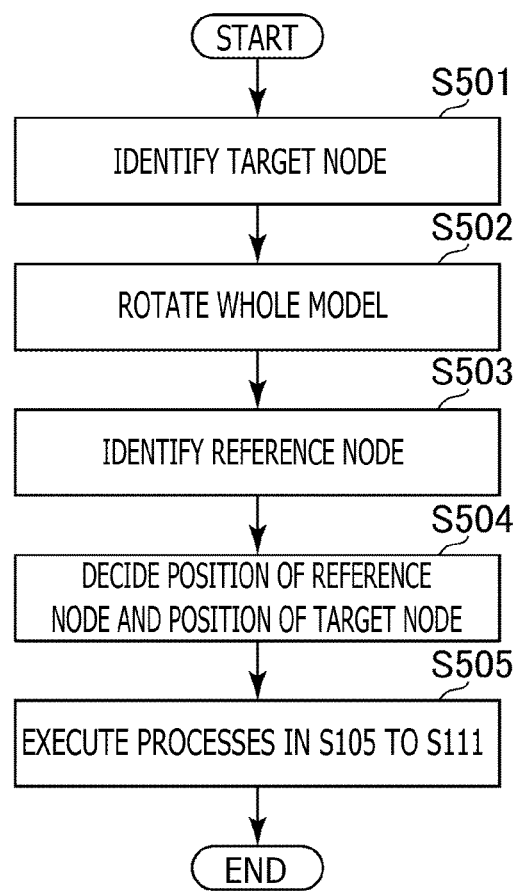
FIG. 20 is a flowchart illustrating one example of a process flow that is executed by an entertainment apparatus according to one embodiment of the present invention.

Here, one example of a process flow which is executed in the entertainment apparatus 14 according to the present embodiment will be explained with reference to a flowchart illustrated in FIG. 20.

In the present process example, it is assumed that the skeleton model 40 being in a pose other than the known standard pose, which is illustrated in FIG. 17, is preliminarily stored in the skeleton model data storage section 50. In addition, it is assumed that a user is allowed to perform operation input to the entertainment apparatus 14 through a controller that is communicable with the entertainment apparatus 14.

First, the target node identifying section 80 identifies target nodes selected by a user's selection operation (S501). Here, for example, the head node 42a, the left hand node 42b, the right hand node 42c, the left foot node 42d, and the right foot node 42e are identified as target nodes.

Next, the pose updating section 56 rotates the entire skeleton model 40 such that a direction from the left foot node 42d toward the right foot node 42e matches with the right-handed axis of a coordinate system (S502). It is to be noted that, it is assumed that, in the following explanation, a given direction in which the head node 42a is disposed with respect to a straight line connecting the left foot node 42d and the right foot node 42e is an upward direction.

Subsequently, the reference node identifying section 82 identifies a reference node (S503). For example, the pelvis node 42f and the third spine node 42i are identified as reference nodes, as previously explained.

Then, the position deciding section 84 decides the positions of the reference nodes and the positions of the target nodes (S504).

For example, here, the position of the pelvis node 42f is decided such that relative positions of the left foot node 42d and the right foot node 42e which are target nodes with respect to the position of the pelvis node 42f which is a reference node are adjusted to predetermined positions. Specifically, for example, a center position x1 between the position of the left foot node 42d and the position of the right foot node 42e is identified. Then, a position that is directly above the position x1 and at a distance of the sum L1 of the lengths of the bone 44t, the bone 44s, and the bone 44r from the position x1 is decided as a position x2 of the pelvis node 42f. Alternatively, a position that is directly above the position x1 and at a distance of the sum L2 of the lengths of the bone 44p, the bone 44o, and the bone 44n from the position x1 may be decided as the position x2 of the pelvis node 42f. Alternatively, a position that is directly above the position x1 and at a distance of the average of the sum L1 and the sum L2 from the position x1 may be decided as the position x2 of the pelvis node 42f.

Further, a position that is directly above the position x2 and at a distance of the length of the bone 44a from the position x2 may be decided as a position x3 of the first spine node 42g. Further, a position that is directly above the position x3 and at a distance of the length of the bone 44b from the position x3 may be decided as a position x4 of the second spine node 42h. Further, a position that is directly above the position x4 and at a distance of the length of the bone 44c from the position x4 may be decided as a position x5 of the third spine node 42i. Further, a position that is directly above the position x5 and at a distance of the length of the bone 44d from the position x5 may be decided as a position x6 of the neck node 42j. Further, a position that is directly above the position x6 and at a distance of the length of the bone 44e from the position x6 may be decided as a position x7 of the head node 42a which is a target node.

Then, for example, the positions of the left hand node 42b and the right hand node 42c are decided such that relative positions of the left hand node 42b and the right hand node 42c, which are target nodes, with respect to the position of the third spine node 42i, which is a reference node, are adjusted to predetermined positions.

For example, the positions of the left hand node 42b and the right hand node 42c are decided such that relative positions of the left hand node 42b and the right hand node 42c with respect to the position of the third spine node 42i, which is a reference node, are adjusted to predetermined positions.

Specifically, for example, a position x8 that is directly above the position x5 of the third spine node 42i and at a distance of a predetermined length L3 from the position x5 may be identified. Further, a position that is at a distance of the sum L4 of the lengths of the bone 44j, the bone 44k, the bone 44l, and the bone 44m, in a positive direction along the right-handed axis of the coordinate system, from the positions x8 may be decided as a position x9 of the right hand node 42c. Further, a position that is at a distance of the sum L5 of the lengths of the bone 44f, the bone 44g, the bone 44h, and the bone 44i, in a negative direction along the right-handed axis of the coordinate system, from the position x9 may be decided as a position x10 of the left hand node 42b.

It is to be noted that, here, the position of the right collarbone node 42n may be identified such that a relative position of the right collarbone node 42n with respect to the position of the third spine node 42i is identical to that in the default pose. Further, a position that is at a distance of the sum L6 of the lengths of the bone 44k, the bone 44l, and the bone 44m, in a positive direction along the right-handed axis of the coordinate system, from the position of the right collarbone node 42n may be decided as the position x9 of the right hand node 42c. Further, the position of the left collarbone node 42k may be identified such that the relative position of the left collarbone node 42k with respect to the position of the third spine node 42i is identical to that in the default pose. Further, a position that is at a distance of the sum L7 of the lengths of the bone 44g, the bone 44h, and the bone 44i, in a negative direction along the right-handed axis of the coordinate system, from the position of the left collarbone node 42k may be decided as the position x10 of the left hand node 42b.

Then, the pose updating section 56 executes the processes illustrated in in S105 to S111 (S505), and then, the process of the present process example is ended.

In the present embodiment, the amount of a manual work to change the skeleton model 40 to a known standard pose is reduced in the abovementioned manner. Thus, according to the present embodiment, time and effort for changing the pose of the skeleton model 40 to a known standard pose can be reduced.

In the above example, a T-pose is adopted as the known standard pose, but any other pose such as an A-pose may be adopted as the known standard pose.

In this case, a position x11 that is directly above the position x5 of the third spine node 42i and at a distance of a predetermined length L8 from the position x5 may be identified in the process illustrated in S504, for example. Further, a position that is at a distance of the sum L4 of the lengths of the bone 44j, the bone 44k, the bone 44l, and the bone 44m, in a positive direction along the right-handed axis of the coordinate system, from the position x11 may be decided as the position x9 of the right hand node 42c. Further, a position that is at a distance of the sum L5 of the lengths of the bone 44f, the bone 44g, the bone 44h, and the bone 44i, in a negative direction along the right-handed axis of the coordinate system, from the position x11 may be decided as the position x10 of the left hand node 42b.

The skeleton model 40 having the same structure as that illustrated in FIG. 3 has been explained in the present process example. However, the present embodiment is also applicable to the skeleton model 40 having a structure different from that illustrated in FIG. 3. For example, the present embodiment is applicable to the skeleton model 40 modeling a dragon with wings. In this case, for example, if a node of a hand of the dragon is identified as a target node, body tracking in which the hand of the dragon moves in conjunction with a motion of a user's hand can be performed. In addition, for example, if a node of a wing of the dragon is identified as a target node, body tracking in which the wing of the dragon moves in conjunction with a motion of a user's hand can be performed. Thus, according to the present embodiment, a target node to move in conjunction with a motion of a tracker 12 in the body tracking can freely be determined.

In addition, it is assumed that a left wrist node corresponding to the left wrist is further included in the skeleton model 40. The left wrist node here may be positioned between the left hand node 42b and the left forearm node 42m, and may be connected to the left hand node 42b and the left forearm node 42m via a bone, for example. In this case, after the process illustrated in S505 is completed, the pose updating section 56 may apply, to rotation of the left hand node 42b, rotation of the left wrist node made after the processes illustrated in S501 to S505 with respect to the left wrist node in a default pose.

Also, in a case where a right wrist node corresponding to the right wrist is further included in the skeleton model 40, rotation of the right wrist node made after the processes illustrated in S501 to S505 with respect to the right wrist node in a default pose may be applied to rotation of the right hand node 42c. The right wrist node here may be positioned between the right hand node 42c and the right forearm node 42p, and may be connected to the right hand node 42c and the right forearm node 42p via a bone, for example.

In addition, right hand finger nodes may be further included in the skeleton model 40. These finger nodes are connected to the right hand node 42c via bones, for example. In this case, after the process illustrated in S505 is completed, the pose updating section 56 may rotate at least one of the bones such that the direction from the position of the right hand node 42c toward the right-hand middle finger node matches with the positive direction of the right-handed axis of the coordinate system and the direction from the position of the right-hand little finger node toward the position of the right-hand thumb node matches with the frontal axis of the coordinate system.

Also, left hand finger nodes may be further included in the skeleton model 40. These finger nodes are connected to the left hand node 42b via bones, for example. In this case, after the process illustrated in S505 is completed, the pose updating section 56 may rotate at least one of the bones such that the direction from the position of the left hand node 42b toward the left-hand middle finger node matches with the negative direction of the right-handed axis of the coordinate system and the direction from the position of the left-hand little finger node toward the position of the left-hand thumb node matches with the frontal axis of the coordinate system.

In the present embodiment, time and effort for changing the pose of the skeleton model 40 to a known standard pose can be reduced in the abovementioned manner.

In addition, in the present embodiment, irrespective of the orientation, the pose, the number of joints, and the shape of the skeleton model 40, the pose of the skeleton model 40 can be changed to a known standard pose. The present embodiment is applicable to the skeleton model 40 of any type that is not facing front, that has arms not open in the horizontal direction, that is crawling on all fours, that is in a lying position, that has many leg joints, that has wings or a tail, that is in a form of a squid, an octopus, or a tree, for example.

In addition, the present embodiment can be used for application of retargeting in which an existing animation is applied to a separate model. According to the present embodiment, retargeting to a variety of models can be achieved. Thus, an existing animation can easily be used.

According to the existing technology, retargeting does not work well unless an animation and the shape of the skeleton model 40 are close to each other to a certain extent. For example, if a human body animation is used, the skeleton model 40 needs to be a human body model. However, according to the present embodiment, retargeting can be implemented in a more versatile and more dynamic manner. A new model can be operated by the present embodiment applied to the model immediately after the model is obtained.

It is to be noted that the present invention is not limited to the abovementioned embodiment.

For example, the application range of the present invention is not limited to real-time updating of the pose of the skeleton model 40 depending on actual movements of trackers 12. For example, the present invention may be applied to a situation in which a motion of the skeleton model 40 or a player object corresponding to the skeleton model 40 is reproduced on the basis of a series of time-series pose data preliminarily stored in the entertainment apparatus 14.

For example, a head mounted display (HMD) may be used as the tracker 12a. In this case, a video may be displayed on a display part of the HMD, for example, according to a result of various processes such as a game process based on the positions or orientations of multiple parts of a user.

Further, for example, some or all of the functions illustrated in FIG. 6 may be implemented by the trackers 12.

Furthermore, specific characters and numerical values in the above explanation and specific characters and numerical values in the drawings are examples. The present invention is not limited to these characters and numerical values.

The invention claimed is:

1. A skeleton model updating apparatus comprising:
circuitry configured to:
identify a plurality of target nodes from among a plurality of nodes included in a skeleton model that is in a pose other than a known standard pose;
identify a reference node positioned closest to a side of the plurality of target nodes, from among nodes connected to all of the plurality of target nodes via one or more bones;
decide positions of the plurality of target nodes or a position of the reference node such that relative positions of the plurality of target nodes with respect to the position of the reference node are adjusted to predetermined positions; and
update the pose of the skeleton model to the standard pose on a basis of the decided positions of the plurality of target nodes.

2. The skeleton model updating apparatus according to claim 1, wherein
the circuitry identifies, as the plurality of target nodes, a node corresponding to a left hand and a node corresponding to a right hand.

3. The skeleton model updating apparatus according to claim 1, wherein
the circuitry identifies, as the plurality of target nodes, a node corresponding to a left hand, a node corresponding to a right hand, and a node corresponding to a head part.

4. The skeleton model updating apparatus according to claim 1, wherein
the circuitry identifies, as the plurality of target nodes, a node corresponding to a left foot and a node corresponding to a right foot.

5. A skeleton model updating method comprising:
identifying a plurality of target nodes from among a plurality of nodes included in a skeleton model that is in a pose other than a known standard pose;
identifying a reference node that is positioned closest to a side of the plurality of target nodes, from among nodes that are connected to all of the plurality of target nodes via one or more bones;
deciding positions of the plurality of target nodes or a position of the reference node such that relative positions of the plurality of target nodes with respect to the position of the reference node are adjusted to predetermined positions; and
updating the pose of the skeleton model to the standard pose on a basis of the decided positions of the plurality of target nodes.

6. A non-transitory computer-readable storage medium storing executable instructions, which when executed by circuitry, causes the circuitry to perform a method, the method comprising:
identifying a plurality of target nodes from among a plurality of nodes included in a skeleton model that is in a pose other than a known standard pose;
identifying a reference node that is positioned closest to a side of the plurality of target nodes, from among nodes that are connected to all of the plurality of target nodes via one or more bones;
deciding positions of the plurality of target nodes or a position of the reference node such that relative positions of the plurality of target nodes with respect to the position of the reference node are adjusted to predetermined positions; and updating the pose of the skeleton model to the standard pose on a basis of the decided positions of the plurality of target nodes.

7. The skeleton model updating apparatus according to claim 1, wherein the standard pose is an A-pose.

8. The skeleton model updating apparatus according to claim 1, wherein the standard pose is a T-pose.

9. The skeleton model updating apparatus according to claim 4, wherein a pelvis node is identified as the reference node for the left foot node and the right foot node.

10. The skeleton model updating apparatus according to claim 3, wherein a spine node is identified as the reference node for the head node, left hand node, and the right hand node.

11. The skeleton model updating method of claim 5, further comprising:
identifying, as the plurality of target nodes, a node corresponding to a left hand and a node corresponding to a right hand.

12. The skeleton model updating method of claim 5, further comprising:
identifying, as the plurality of target nodes, a node corresponding to a left hand, a node corresponding to a right hand, and a node corresponding to a head part.

13. The skeleton model updating method of claim 5, further comprising:
identifying, as the plurality of target nodes, a node corresponding to a left foot and a node corresponding to a right foot.

14. The skeleton model updating method of claim 13, wherein a pelvis node is identified as the reference node for the left foot node and the right foot node.

15. The skeleton model updating method of claim 12, wherein a spine node is identified as the reference node for the node corresponding to the head part, the left hand node, and the right hand node.

16. The non-transitory computer-readable storage medium of claim 6, the method further comprising:
identifying, as the plurality of target nodes, a node corresponding to a left hand and a node corresponding to a right hand.

17. The non-transitory computer-readable storage medium of claim 6, the method further comprising:
identifying, as the plurality of target nodes, a node corresponding to a left hand, a node corresponding to a right hand, and a node corresponding to a head part.

18. The non-transitory computer-readable storage medium of claim 6, the method further comprising:
identifying, as the plurality of target nodes, a node corresponding to a left foot and a node corresponding to a right foot.

19. The non-transitory computer-readable storage medium of claim 18, wherein a pelvis node is identified as the reference node for the left foot node and the right foot node.

20. The non-transitory computer-readable storage medium of claim 17, wherein a spine node is identified as the reference node for the node corresponding to the head part, the left hand node, and the right hand node.

* * * * *